US008729273B2

(12) United States Patent
Song et al.

(10) Patent No.: US 8,729,273 B2
(45) Date of Patent: May 20, 2014

(54) COMPOUNDS EFFECTIVE AS XANTHINE OXIDASE INHIBITORS, METHOD FOR PREPARING THE SAME, AND PHARMACEUTICAL COMPOSITION CONTAINING THE SAME

(75) Inventors: Jeong Uk Song, Daejeon (KR); Geun Tae Kim, Daejeon (KR); Sung Pil Choi, Daejeon (KR); Cheol Kyu Jung, Daejeon (KR); Deok Seong Park, Daejeon (KR); Eun Sil Choi, Daejeon (KR); Tae Hun Kim, Daejeon (KR); Hyun Jung Park, Daejeon (KR); Wan Su Park, Daejeon (KR); Heui Sul Park, Daejeon (KR); Ki Chul Koo, Daejeon (KR); Vasily Artemov, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 13/498,253

(22) PCT Filed: Oct. 4, 2010

(86) PCT No.: PCT/KR2010/006760
§ 371 (c)(1),
(2), (4) Date: Mar. 26, 2012

(87) PCT Pub. No.: WO2011/043568
PCT Pub. Date: Apr. 14, 2011

(65) Prior Publication Data
US 2012/0184582 A1    Jul. 19, 2012

(30) Foreign Application Priority Data
Oct. 7, 2009  (KR) .................. 10-2009-0095363

(51) Int. Cl.
*C07D 403/02*    (2006.01)
*A61K 31/4427*   (2006.01)

(52) U.S. Cl.
USPC ...................................... 548/312.1; 514/339

(58) Field of Classification Search
None
See application file for complete search history.

(56) References Cited

U.S. PATENT DOCUMENTS

| 2008/0114006 | A1 | 5/2008 | Flynn et al. |
| 2009/0018104 | A1 | 1/2009 | Sato et al. |
| 2010/0056521 | A1 | 3/2010 | Shimizu et al. |

FOREIGN PATENT DOCUMENTS

| EP | 2338887 A1 | 6/2011 | | |
| WO | WO 02/04440 A1 | * | 1/2002 | |
| WO | WO 2007/043457 A1 | | 4/2007 | |
| WO | WO 2008011131 A2 | * | 1/2008 | ............ C07D 401/12 |
| WO | WO 2008034008 A2 | * | 3/2008 | ......... A61K 31/4375 |
| WO | WO 2008/126898 A1 | | 10/2008 | |
| WO | WO 2010/045186 A1 | | 4/2010 | |

OTHER PUBLICATIONS

International Search Report, PCT/KR2010/006760, Jun. 29, 2011.
Bhayana et al., "A Versatile Catalyst System for Suzuki-Miyaura Cross-Coupling Reactions of C(sp2)-Tosylates and Masylates." Organic Letters, vol. 17, 2009 (published on web Aug. 10, 2009), pp. 3954-3957.
Billingsley et al., "Highly Efficient Monophosphirse-Based Catalyst for the Palladium-Catalyzed Suzuki-Miyaura Reaction of Heteroaryl Halides and Heteroaryl Boronic Acids and Esters." Journal of the American Chemical Society, vol. 129, 2007 (published on web Feb. 28, 2007), pp. 3358-3366.
Doll, "A Short Synthesis of the 8-Azaergoline Ring System by Intramolecular Tandem Decarboxylation-Cyclization of the Minisci-Type Reaction." Journal of Organic Chemistry, vol. 64, 1999 (published on web Jan. 30, 1999), pp. 1372-1374.

* cited by examiner

*Primary Examiner* — Brandon Fetterolf
*Assistant Examiner* — Ana Z Muresan
(74) *Attorney, Agent, or Firm* — Birch, Stewart, Kolasch & Birch, LLP

(57) ABSTRACT

The present invention relates to novel compounds which are effective as an inhibitor for xanthine oxidase, a process for preparing the same, and a pharmaceutical composition comprising a therapeutically effective amount of the same.

15 Claims, 1 Drawing Sheet

COMPOUNDS EFFECTIVE AS XANTHINE OXIDASE INHIBITORS, METHOD FOR PREPARING THE SAME, AND PHARMACEUTICAL COMPOSITION CONTAINING THE SAME

TECHNICAL FIELD

The present invention relates to novel compounds of formula (1):

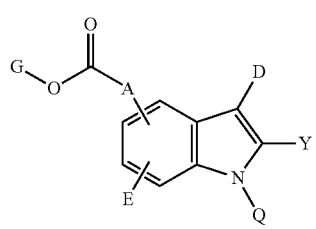

(1)

in which
A, D, E, G, Y and Q are as defined below, which are effective as an inhibitor for xanthine oxidase, a process for preparing the same, and a pharmaceutical composition comprising a therapeutically effective amount of the same.

BACKGROUND ART

Xanthine oxidase is known as an enzyme which converts hypozanthine to xanthine and further converts thus-formed zanthine to uric acid. Although most mammals have uricase, humans and chimpanzees do not, thereby uric acid is known to be the final product of purine metabolism (S. P. Bruce, Ann. Pharm., 2006, 40, 2187~2194). Sustained elevation of blood concentration of uric acid causes various diseases, representatively including gout.

As described above, gout is caused by an elevated level of uric acid in the body, indicating the condition in which uric acid crystals accumulated in cartilage, ligament and surrounding tissue induce severe inflammation and pain. Gout is a kind of inflammatory articular disease, and its incidence rate has steadily increased during past 40 years (N. L. Edwards, Arthritis & Rheumatism, 2008, 58, 2587~2590).

From the 1960s to the mid-1990s, gout patients in the West exhibited an astonishing increase of about 200~300%, mainly in males. The increased rate of gout patients can be traced to obesity, aging, kidney function decline, hypertension, etc. The incidence rate of gout appears to be a level of about 1.4/1,000 persons, but it also depends on the uric acid level. That is, while the incidence rate of gout is 0.5% in a patient group with a blood uric acid level of 7.0 mg/dl or more, the incidence rate of gout is 5.5% in a patient group with a uric acid level of 9.0 mg/dl or more (G. Nuki, Medicine, 2006, 34, 417~423). Considering the incidence rate as described above, blood uric acid level is found to be an important causative factor for gout. In addition, dietary habits, alcohol, lipid and obesity can serve as important inducing factors of gout. Recently, the correlation of uric acid with heart failure, hypertension, diabetes, kidney diseases and cardiovascular diseases has been extensively investigated by many researchers, and the importance of uric acid control has been increased (D. I. Feig et al., N. Eng. J. Med, 2008, 23, 1811~1821). In addition, as an inhibitor of xanthine oxidase, allopurinol is known to have an effect on ulcerative colitis (Aliment. Pharmacol. Ther. 2000, 14, 1159~1162; WO 2007/043457).

Allopurinol was a unique drug for the treatment of gout for 40 years, until febuxostat was approved as an arthrifuge in USA in 2009 (Brain Tomlinson, Current Opin. Invest. Drugs, 2005, 6, 1168~1178). Allopurinol is known to be a non-specific inhibitor for various enzymes that are involved in purine and pyrimidine metabolism, and it has a Ki of 700 nM for xanthine oxidase (Y. Takano et al., Life Sciences, 2005, 76, 1835~1847). Allopurinol is immediately oxidized to oxypurinol by xanthine oxidase, and this metabolite is known to act as a potent inhibitor for xanthine oxidase.

However, it is known that allopurinol causes gastrointestinal side effects and skin rash and exhibits poor compliance in the case of long-term administration. Especially among patients receiving allopurinol, the side effect of Stevens-Johnson syndrome is reported, at a low rate but it is unpredictable and lethal (Felix Arellano et al., Ann. Pharm., 1993, 27, 337~43). This serious side effect is known to accompany necrocytosis in the skin and mouth mucosa, and without proper treatment about 25% of patients may die as a result.

Thus, in order to develop novel xanthine oxidase inhibitors various researches have been conducted resulting in numerous patent publications (for example, WO 1992/009279, WO 1998/018765, WO 2007/004688, WO 2007/043457, WO 2008/126770, WO 2008/126898, WO 2008/126899).

Among these, WO 1998/018765 describes the inhibitory effect of pyrazoles and phenyl derivatives against xanthine oxidase, and WO 2008/126898 reports that indole compounds exhibit an inhibitory effect against xanthine oxidase.

DISCLOSURE OF INVENTION

Technical Problem

One object of the present invention is to provide novel compounds of formula (1) which exhibit very excellent inhibitory effect against xanthine oxidase.

Another object of the present invention is to provide a novel process for the preparation of the compounds of formula (1).

Still another object of the present invention is to provide a pharmaceutical composition for the inhibition of xanthine oxidase, which comprises a therapeutically effective amount of the compounds of formula (1) as an active ingredient.

Still another object of the present invention is to provide a method for the treatment and/or prevention of the diseases associated with xanthine oxidase such as hyperuricemia, gout, heart failure, cardiovascular disease, hypertension, diabetes, kidney disease, inflammation and articular disease, and inflammatory bowel disease, which comprises using the compounds of formula (1) as an active ingredient.

Solution to Problem

In order to solve the above stated technical subject, the present invention provides the compounds of the following formula (1):

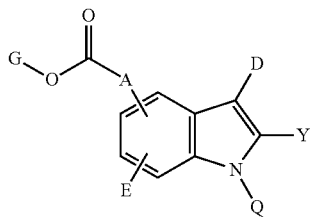

(1)

in the above formula (1)

A is selected from the following substituents A-i, A-ii, A-iii, A-iv, A-v, A-vi, A-vii and A-viii:

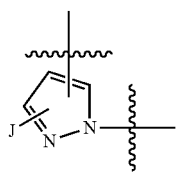

(A-i)

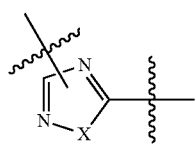

(A-ii)

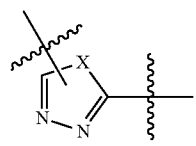

(A-iii)

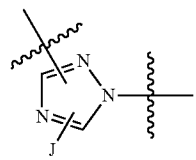

(A-iv)

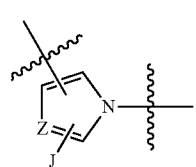

(A-v)

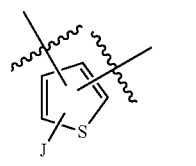

(A-vi)

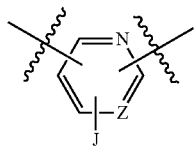

(A-vii)

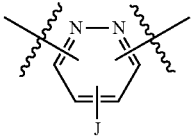

(A-viii)

wherein
J represents hydrogen, halogen, or halogen-substituted or unsubstituted $C_1$-$C_6$-alkyl, preferably $C_1$-$C_4$-alkyl,
X represents O or S,
Z represents C or N,
E represents hydrogen, halogen, cyano, nitro, substituted or unsubstituted $C_1$-$C_6$-alkyl, or substituted or unsubstituted $C_1$-$C_6$-alkoxy,
D represents hydrogen, halogen, cyano, nitro, halogen-substituted or unsubstituted $C_1$-$C_6$-alkyl, —CHO, or —CH=N—OH,
Q is selected from the following substituents Q-i, Q-ii and Q-iii-1 to Q-iii-9:
(Q-i) hydrogen;
(Q-ii) substituted or unsubstituted, saturated or unsaturated, and straight-chain, branched or cyclic alkyl;

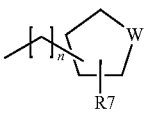

(Q-iii-1)

(wherein W represents O or S, R7 represents hydrogen, or substituted or unsubstituted lower alkyl, and n denotes an integer of 0~3);

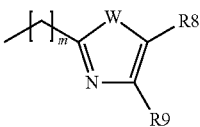

(Q-iii-2)

(wherein W represents O or S, R8 and R9 each represent hydrogen or lower alkyl, and m denotes an integer of 1~3);

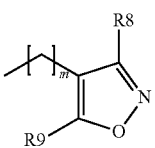

(Q-iii-3)

(wherein R8 and R9 each represent hydrogen or lower alkyl, and m denotes an integer of 1~3);

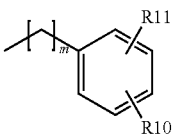

(Q-iii-4)

(wherein R10 and R11 each represent hydrogen, halogen, lower alkoxy or lower alkyl, and m denotes an integer of 1~3);

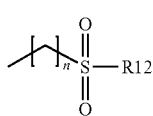
(Q-iii-5)

(wherein R12 represents substituted or unsubstituted lower alkyl or aromatic group, and n denotes an integer of 0~3);

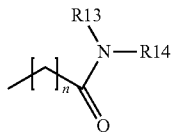
(Q-iii-6)

(wherein R13 and R14 each represent substituted or unsubstituted lower alkyl, or together with N to which they are attached may form a 3~7 membered heterocycle, and n denotes an integer of 0~3);

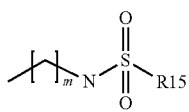
(Q-iii-7)

(wherein R15 represents substituted or unsubstituted lower alkyl, and m denotes an integer of 1~3);

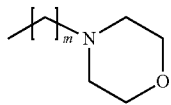
(Q-iii-8)

(wherein m denotes an integer of 1~3);

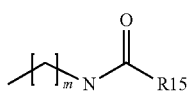
(Q-iii-9)

(wherein R15 represents substituted or unsubstituted lower alkyl, and m denotes an integer of 1~3);

Y represents hydrogen, halogen, substituted or unsubstituted, saturated or unsaturated, and straight-chain, branched or cyclic alkyl, substituted or unsubstituted $C_1$-$C_6$-alkoxy, or substituted or unsubstituted aromatic or heteroaromatic group, and G represents hydrogen, or represents substituted or unsubstituted, saturated or unsaturated, and straight-chain, branched or cyclic alkyl.

Hereinafter, unless specially restricted, the compounds of formula (1) as an active ingredient of the therapeutic agent include all their pharmaceutically acceptable salts and isomers, and they should be instructed to fall under the scope of the present invention. For the convenience of explanation only, they are simply referred to as 'compounds of formula (1)' in the present specification.

The above compounds of formula (1) according to the present invention have a quite different chemical structure from the earlier known xanthine oxidase inhibitors. As shown in the following experiments, they exhibit an excellent inhibitory effect against xanthine oxidase associated with gout. Thus, they can be used for the prevention and treatment of diseases associated with xanthine oxidase, such as, for example, hyperuricemia, heart failure, cardiovascular disease, hypertension, diabetes, kidney disease, inflammation, articular disease, etc.

The terms as used herein will be briefly explained below.

If there is no special mention in the present specification, the term "substituted or unsubstituted" means to include both the cases of being substituted and unsubstituted. In the case of "substituted," the radical may be substituted individually and independently by one or more groups selected from alkyl, cycloalkyl, hydroxy, alkoxy, mercapto, alkylthio, cyano, halogen, carbonyl, thiocarbonyl, nitro and their protective derivatives. If appropriate, these groups may be furthermore substituted.

As used herein, "pharmaceutically acceptable salts" means the salt forms of a compound, which neither give any serious irritation to the organism to which the compound is administered nor damage the biological activities and properties of the compound. Such a "pharmaceutically acceptable salt" includes a non-toxic acid addition salt containing a pharmaceutically acceptable anion, for example, a salt with inorganic acids such as hydrochloric acid, sulfuric acid, nitric acid, phosphoric acid, hydrobromic acid, hydriodic acid, etc.; a salt with organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, etc.; or a salt with sulfonic acids such as methanesulfonic acid, ethanesulfonic acid, benzenesulfonic acid, p-toluenesulfonic acid, etc. The compounds of formula (1) can also form a pharmaceutically acceptable salt, for example, a salt with alkali metals or alkaline earth metals such as lithium, sodium, potassium, calcium, magnesium, etc.; a salt with amino acids such as lysine, arginine, guanidine, etc.; or an organic salt with dicyclohexylamine, N-methyl-D-glucamine, tris(hydroxymethyl)methylamine, di-ethanolamine, choline, triethylamine, etc. The compounds of formula (1) of the present invention may be converted to their salts according to any of the conventional methods.

As used herein, "isomer" means those having the same chemical or molecular formula as, but optically or sterically different from, the compounds of formula (1), or salts thereof. The compounds of formula (1) of the present invention may have an oxime structure, and so may exist in the form of geometrical isomers, trans and cis. All the isomers, their salts, and their mixtures (including racemic mixture) are also covered by the present invention.

As used herein, "aromatic" means a carbocyclic aryl (e.g., phenyl, naphthyl, etc.) group having a covalent π electronic system and at least one ring. This term also includes monocyclic or fused-ring polycyclic (i.e., rings sharing the adjacent carbon pairs) groups.

As used herein, "heteroaromatic" means a heterocyclic aryl group having a covalent π electronic system and at least one ring. It includes but is not limited to furan, thiophene, pyrrole, oxazole, thiazole, imidazole, pyrazole, isothiazole, triazole, thiadiazole, pyridine, pyridazine, pyrimidine, pyrazine, triazine, etc.

As used herein, "alkyl" means an aliphatic hydrocarbon group. The alkyl group may be "a saturated alkyl" not containing alkene or alkine moiety at all, or "an unsaturated alkyl" containing at least one alkene or alkine moiety. The term "alkene" means a group having at least one carbon-carbon double bond, and "alkine" means a group having at least one carbon-carbon triple bond. Regardless of being saturated or unsaturated, the alkyl group may be branched, linear or cyclic.

Unless otherwise stated, the alkyl group may contain 1 to 20 carbon atoms, and the lower alkyl group may contain 1 to 7 carbon atoms. As typical examples thereof, methyl, ethyl, propyl, isopropyl, butyl, isobutyl, t-butyl, pentyl, hexyl, ethenyl, propenyl, butenyl, ethinyl, propinyl, butinyl, cyclopropyl, cyclobutyl, cyclopentyl, cyclohexyl, etc. can be mentioned. The alkyl group may be substituted or unsubstituted. In the case of "substituted," the radical may be substituted individually and independently by one or more groups selected from cycloalkyl, hydroxy, alkoxy, mercapto, alkylthio, cyano, halogen, carbonyl, thiocarbonyl, nitro and their protective derivatives.

As used herein, "heterocycle" means a group wherein the ring carbon atom is replaced by oxygen, nitrogen, sulfur, etc. It may optionally include a double bond. The typical examples thereof may include but are not limited to pyrroline, pyrrolidine, imidazoline, imidazolidine, pyrazoline, pyrazolidine, pyran, piperidine, morpholine, thiomorpholine, piperazine, etc.

As used herein, "halogen (or halo)" means F (or —F), Cl (or —Cl), Br (or —Br) and I (or —I).

Other terms in the present specification may be construed to have the meaning conventionally understood in this field by a skilled artisan.

Preferred compounds among the compounds of formula (1) above are those wherein Q is selected from the following substituents Q-i to Q-iii-8:

(Q-i) hydrogen;

(Q-ii) $C_1$-$C_8$-alkyl which is unsubstituted or substituted by a group selected from halogen, hydroxy, $C_3$-$C_7$-cycloalkyl and O—$R_6$ wherein $R_6$ represents $C_1$-$C_7$-alkyl;

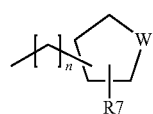
(Q-iii-1)

(wherein W represents O or S, R7 represents hydrogen, or substituted or unsubstituted lower alkyl, and n denotes an integer of 0~3);

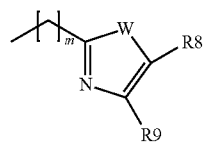
(Q-iii-2)

(wherein W represents O or S, R8 and R9 each represent hydrogen or lower alkyl, and m denotes an integer of 1~3);

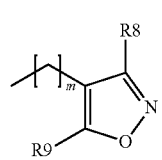
(Q-iii-3)

(wherein R8 and R9 each represent hydrogen or lower alkyl, and m denotes an integer of 1~3);

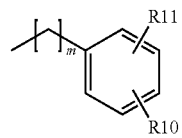
(Q-iii-4)

(wherein R10 and R11 each represent hydrogen, halogen, lower alkoxy or lower alkyl, and m denotes an integer of 1~3);

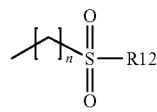
(Q-iii-5)

(wherein R12 represents substituted or unsubstituted lower alkyl or aromatic group, and n denotes an integer of 0~3);

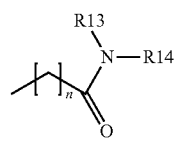
(Q-iii-6)

(wherein R13 and R14 each represent substituted or unsubstituted lower alkyl, or together with N to which they are attached may form a 3~7 membered heterocycle, and n denotes an integer of 0~3);

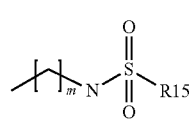
(Q-iii-7)

(wherein R15 represents substituted or unsubstituted lower alkyl, and m denotes an integer of 1~3);

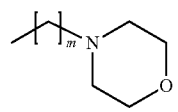
(Q-iii-8)

(wherein m denotes an integer of 1~3).

Also preferred compounds are those wherein A is selected from the following substituents A-i, A-ii, A-iii, A-iv, A-v, A-vi, A-vii and A-viii:

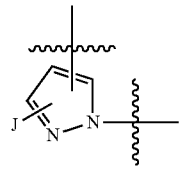
(A-i)

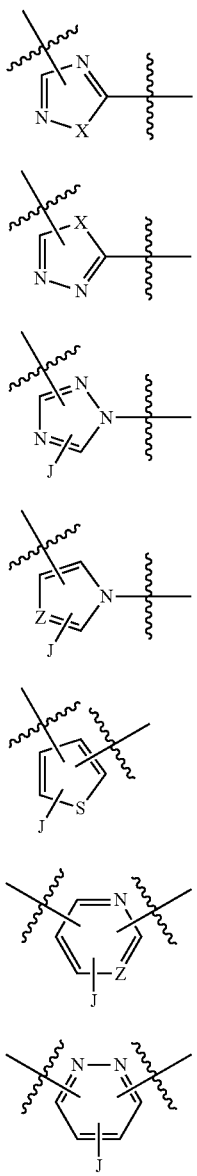

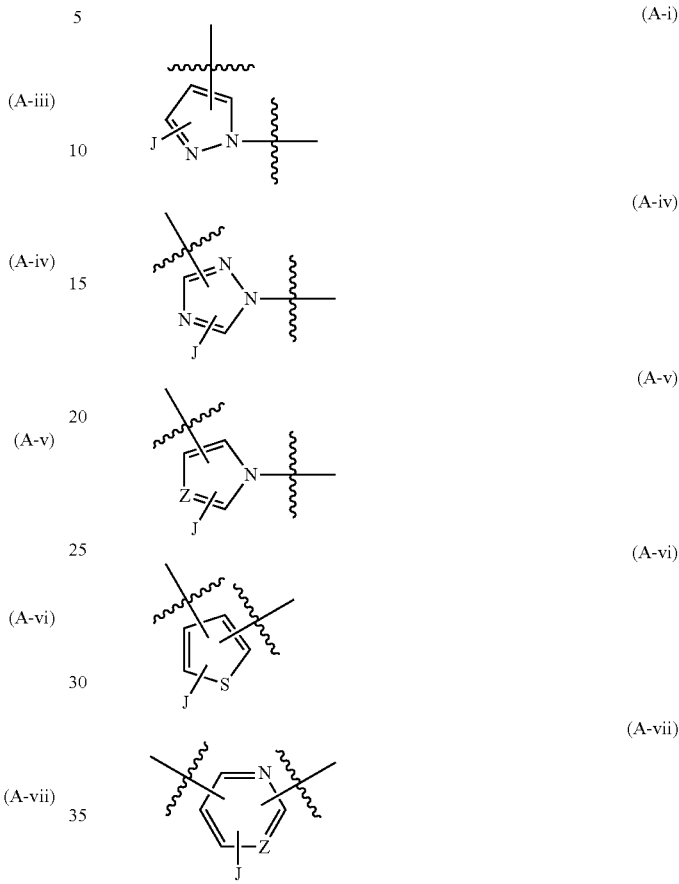

wherein

J represents halogen-substituted or unsubstituted $C_1$-$C_4$-alkyl,

X represents O or S, and

Z represents C or N.

In the preferred compounds of formula (I), E represents hydrogen, halogen, cyano or nitro.

In the preferred compounds of formula (I), D represents halogen, cyano, nitro, or —CHO.

In the preferred compounds of formula (I), Y represents hydrogen, $C_1$-$C_7$-alkyl, $C_1$-$C_7$-alkoxy-$C_1$-$C_7$-alkyl, or aromatic group.

In the preferred compounds of formula (I), G represents hydrogen.

Particularly preferred compounds among the preferred compounds of formula (I) are those wherein A is selected from the following substituents A-i, A-iv, A-v, A-vi and A-ii:

wherein

J represents halogen-substituted or unsubstituted $C_1$-$C_4$-alkyl,

X represents O or S, and

Z represents C or N,

E represents hydrogen or cyano,

D represents cyano or nitro,

Q is selected from the following substituents Q-i, Q-ii and Q-iii-1:

(Q-i) hydrogen;

(Q-ii) $C_1$-$C_8$-alkyl which is unsubstituted or substituted by a group selected from halogen, $C_3$-$C_7$-cycloalkyl and O—$R_6$ wherein $R_6$ represents $C_1$-$C_4$-alkyl;

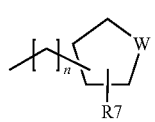
(Q-iii-1)

(wherein W represents O or S, R7 represents hydrogen or $C_1$-$C_4$-alkyl, and n denotes an integer of 0~3);

Y represents hydrogen, $C_1$-$C_4$-alkyl, $C_1$-$C_4$-alkoxy-$C_1$-$C_4$-alkyl or phenyl, and G represents hydrogen.

The representative compounds of formula (1) according to the present invention include the following listed compounds:

1. 1-(3-cyano-1-isopropyl-indol-5-yl)pyrazole-4-carboxylic acid;

2. 1-[3-cyano-1-(cyclopropylmethyl)indol-5-yl]pyrazole-4-carboxylic acid;
3. 1-[3-cyano-1-cyclopropyl-indol-5-yl]pyrazole-4-carboxylic acid;
4. 1-(3-cyano-1-isobutyl-indol-5-yl)pyrazole-4-carboxylic acid;
5. 1-[3-cyano-1-(2,2-dimethylpropyl)indol-5-yl]pyrazole-4-carboxylic acid;
6. 1-[3-cyano-1-(2-methoxyethyl)indol-5-yl]pyrazole-4-carboxylic acid;
7. 1-(3-cyano-1-sec-butyl-indol-5-yl)-pyrazole-4-carboxylic acid;
8. 1-[3-cyano-1-cyclobutyl-indol-5-yl]pyrazole-4-carboxylic acid;
9. 1-(3-cyano-1-cyclopentyl-indol-5-yl)-pyrazole-4-carboxylic acid;
10. 1-[3-cyano-1-(1-fluoropropan-2-yl)-indol-5-yl]-pyrazole-4-carboxylic acid;
11. 1-[3-cyano-1-(tetrahydrofuran-3-yl)-indol-5-yl]-pyrazole-4-carboxylic acid;
12. 1-[3-cyano-1-isopropyl-indol-5-yl]-3-methyl-pyrazole-4-carboxylic acid;
13. 1-[3-cyano-1-(cyclopropylmethyl)indol-5-yl]-3-methyl-pyrazole-4-carboxylic acid;
14. 1-[3-cyano-1-(2-methoxyethyl)indol-5-yl]-3-methyl-pyrazole-4-carboxylic acid;
15. 1-[3-cyano-1-isopropyl-indol-5-yl]-3-(trifluoromethyl)pyrazole-4-carboxylic acid;
16. 1-[3-cyano-1-(cyclopropylmethyl)indol-5-yl]-3-(trifluoromethyl)pyrazole-4-carboxylic acid;
17. 1-(1-isopropyl-3-nitro-indol-5-yl)pyrazole-4-carboxylic acid;
18. 1-(3-cyano-1-isopropyl-indol-5-yl)-1,2,4-triazole-3-carboxylic acid;
19. 1-(3-cyano-1-isopropyl-indol-5-yl)imidazole-4-carboxylic acid;
20. 5-(3-cyano-1-isopropyl-indol-5-yl)-thiophene-2-carboxylic acid;
21. 2-(3-cyano-1-isopropyl-indol-5-yl)isonicotinic acid;
22. 2-[3-cyano-1-(cyclopropylmethyl)-indol-5-yl]isonicotinic acid;
23. 2-[3-cyano-1-(tetrahydrofuran-3-yl)-indol-5-yl]isonicotinic acid;
24. 2-[3-cyano-1-(1-fluoropropan-2-yl)-indol-5-yl]isonicotinic acid;
25. 2-[3-cyano-1-(2-methoxyethyl)-indol-5-yl]isonicotinic acid;
26. 2-(3-cyano-1-isopropyl-indol-5-yl)-6-methylisonicotinic acid;
27. 2-(1-isopropyl-3-nitro-indol-5-yl)isonicotinic acid;
28. 1-(7-cyano-2-phenyl-1H-indol-5-yl)-pyrazole-4-carboxylic acid;
29. 1-(7-cyano-2-isopropyl-1H-indol-5-yl)-pyrazole-4-carboxylic acid;
30. 1-(7-cyano-2-methoxymethyl-1H-indol-5-yl)-pyrazole-4-carboxylic acid; and
31. 1-(7-cyano-1H-indol-5-yl)-pyrazole-4-carboxylic acid.

The present invention also provides processes for preparing the compounds of formula (1). One of ordinary skill in the art to which the present invention pertains ("a skilled artisan") may prepare the compounds of formula (1) via various routes according to their structures, and such processes should be construed to fall under the scope of the present invention. In other words, the compounds of formula (1) may be prepared by optionally combining various synthetic methods which are described in the present specification or disclosed in the prior arts. The processes for preparing the compounds of formula (1) cover even such processes and are not limited to those explained below.

As one typical process, the compounds of formula (1) wherein Q is not hydrogen may be prepared by reacting compounds of formula (2) with compounds of formula (3) in the presence of a base, as depicted in the following Reaction Scheme (1):

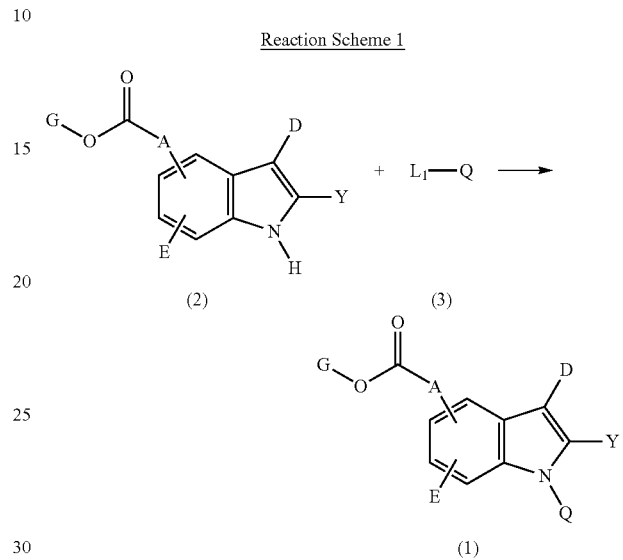

in the above Reaction Scheme (1),

A, D, E, G, Y and Q are as defined for the formula (1) above, provided that Q is not hydrogen, and $L_1$ represents a leaving group in the substitution reaction, such as for example, halogen, methanesulfonyloxy, p-toluenesulfonyloxy, trifluoromethanesulfonyloxy, etc.

The above reaction may be carried out in an organic solvent such as dimethylformamide, dimethylacetamide, acetonitrile, etc., and in some cases a mixture of two or more organic solvents may be used. Typical examples for the base used in the reaction include sodium hydride, sodium hydroxide, potassium t-butoxide, cesium carbonate, potassium carbonate, sodium carbonate, potassium bis(trimethylsilyl)amide, etc., and in some cases a mixture of two or more bases may be used together.

If necessary, when G is not hydrogen, the compounds obtained by the above Reaction Scheme (1) may be hydrolyzed to give the compounds of formula (1) wherein G is hydrogen.

As another typical process, the compounds of formula (1) wherein D is not hydrogen and Q is hydrogen may be prepared by introducing the substituent D according to the following Reaction Scheme (2):

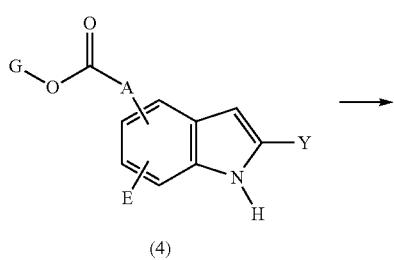

-continued

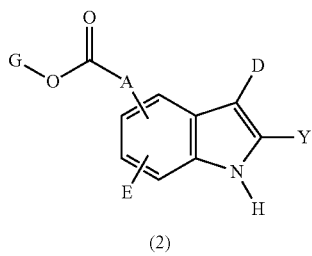

(2)

-continued

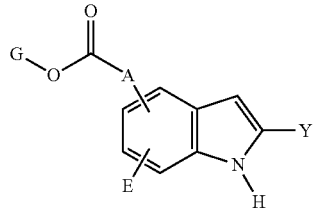

(4)

in the above Reaction Scheme (2),

A, D, E, G and Y are as defined in formula (1), provided that D is not hydrogen.

In the above Reaction Scheme (2), the case wherein D is nitro is explained first as follows.

The compound (4), silver nitrate and benzoyl chloride may be reacted in an organic solvent such as acetonitrile, etc. to give the final Compound (2) wherein D is nitro. Or, Compound (2) wherein D is nitro may also be obtained by using nitric acid and acetic anhydride where, if necessary, a mixture of two or more organic solvents is used (Tetrahedron, 2000, 56, 10133).

If appropriate, the group Q is introduced first to Compound (4) according to Reaction Scheme (1) and then nitro group may be introduced as explained above.

In the above Reaction Scheme (2), the case wherein D is cyano is explained as follows.

The indole Compound (4) is reacted with oxalyl chloride in dichloromethane, tetrahydrofuran and ammonium acetate are added in drops thereto, and the mixture is heated to give an aldehyde compound [Compound (2) wherein D is —CHO]. The aldehyde compound is reacted with hydroxylamine in pyridine solvent to give an oxime compound. The oxime compound is reacted with 2-chloro-1-methyl-pyridinium iodide or di(imidazol-1-yl)methanethione and triethylamine in tetrahydrofuran to give Compound (2) wherein D is —CN. This reaction may be carried out by referring to J. Ludwig et al., J. Med. Chem., 2006, 49, 2611.

If necessary, the substituent Q may be first introduced to Compound (4) in the same manner as the above Reaction Scheme (1), and the cyano group may be introduced later as explained above.

Compound (4) used as a starting material in the above Reaction Scheme (2) may be prepared according to the following Reaction Scheme (3):

Reaction Scheme 3

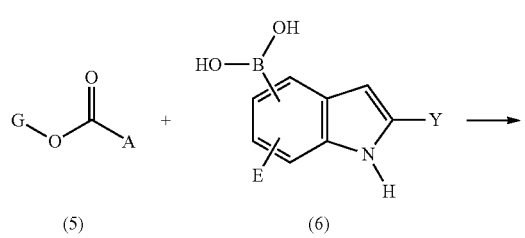

(5)       (6)

in the above Reaction Scheme (3),

A, E, G and Y are as defined in formula (1).

The process for preparing Compound (4) according to the above Reaction Scheme (3) is explained in detail below. Compound (5) and Compound (6) are dissolved together with copper (II) acetate and pyridine in N,N-dimethylformamide or dimethylsulfoxide, and they are reacted to give Compound (4). Alternatively, Compound (5) and Compound (6) are dissolved together with sodium carbonate and tetrakis(triphenylphosphine)palladium in toluene or dioxane, and they are reacted to give Compound (4).

A skilled artisan might also prepare the above reacting compounds by various processes on the basis of their chemical structures under the scope of the present invention.

A skilled artisan could confirm the specific reaction conditions, etc. for the preparation of the compounds according to the present invention through preparations and examples below, and thus their detailed explanations are omitted here.

The present invention further provides a pharmaceutical composition for the inhibition of xanthine oxidase, which comprises (a) a therapeutically effective amount of the compounds of formula (1), pharmaceutically acceptable salts or isomers thereof and (b) pharmaceutically acceptable carriers, diluents, excipients or their combinations.

As used herein, "pharmaceutical composition" means compositions comprising the compounds of the present invention and other chemical components such as carriers, diluents, excipients, etc. A pharmaceutical composition facilitates the administration of the compound into a living organism. There are a number of techniques to administer the compound, and they include but are not limited to oral, injectable, aerosol, parenteral and topical administration. The therapeutically active ingredients to be contained in the pharmaceutical composition may be converted to their salts by reacting acid compounds such as hydrochloric acid, hydrobromic acid, sulfuric acid, nitric acid, phosphoric acid, methanesulfonic acid, p-toluenesulfonic acid, salicylic acid, etc. with the compounds of formula (1).

As used herein, "therapeutically effective amount" means the amount of active ingredient effective to alleviate or remove one or more symptoms of the disorder to be treated, or to delay clinical markers or the initiation of symptoms of the disease to be prevented. Thus, the therapeutically effective amount means the amount having the effect of (1) reversing the rate of progress of the disease, (2) prohibiting further progress of the disease and/or (3) alleviating (preferably, removing) one or more symptoms associated with the disease. The therapeutically effective amount can be determined on the basis of experience by testing compounds in the in vivo and in vitro model systems known for the disease to be treated.

As used herein, "carrier" means a substance that facilitates the incorporation of the compound into cells or tissues. For example, dimethylsulfoxide (DMSO) is a typical carrier that facilitates the introduction of various organic compounds into cells or tissues of living organisms.

As used herein, "diluent" is defined as a substance that is diluted in water, which dissolves the subject compound as well as stabilizes the biologically active form of the compound. The salts dissolved in a buffer solution are utilized as diluents in the art. A typically used buffer solution is phosphate-buffered saline which mimics the salt form of human solution. Buffer diluents rarely alter the biological activities of the compound, as the buffer salts can control the pH of solution at a low concentration.

The compound used herein may be administered as the compound per se or as a pharmaceutical composition comprising the compound with other active ingredients in the combination therapy or with other suitable carriers or excipients, to the human patient. Techniques for formulations and administrations of a compound can be found in "Remington's Pharmaceutical Sciences" (Mack Publishing Co., Easton, Pa., 18$^{th}$ edition, 1990).

The pharmaceutical composition of the present invention may be prepared by known methods, such as, for example, conventional mixing, dissolving, granulating, dragee-preparing, powdering, emulsifying, capsulating, trapping, freeze-drying, etc.

Thus, the pharmaceutical composition of the present invention may be prepared by conventional methods of using one or more pharmaceutically acceptable carriers. The carriers include excipients or adjuvants by which the active compound can be easily converted to pharmaceutically acceptable formulations. Suitable formulations may depend on the selected administration route. Techniques, carriers and excipients, and means known in the art, for example, in "Remington's Pharmaceutical Sciences," as explained above may be appropriately selected.

For example, the compounds of formula (1) of the present invention can be formulated as an injectable preparation, oral preparation, etc., depending on the purpose intended.

As for the injection preparation, the active compounds of the present invention can be formulated to a liquid preparation by using pharmaceutically suitable buffers, preferably Hank solution, Ringer solution, physiological saline, etc. For the purpose of administration through mucous membranes, penetration promoters suitable for the barrier to be penetrated are used for the formulation. Such penetration promoters are conventionally known in the art.

The active compounds of the present invention can be easily formulated as dosage forms for oral administration by combining the compounds with pharmaceutically acceptable carriers known in the art. With the use of such carriers, the compounds of the present invention can be formulated to tablets, pills, powders, granules, dragees, capsules, liquids, gels, syrups, slurries, suspensions, etc. Capsules, tablets, pills, powders and granules are advantageous, and capsules and tablets are particularly advantageous. Preferably, tablets and pills are prepared as enteric coated forms. For example, the solid dosage forms for oral administration can be obtained as follows.

One or more compounds of the present invention are mixed with one or more excipients, and the mixture is pulverized, if appropriate. Suitable adjuvants are added if necessary, and tablets or dragee cores can be obtained from the granule mixtures. As suitable excipients, fillers such as lactose, sucrose, mannitol or sorbitol; cellulose substances such as corn starch, wheat starch, rice starch, potato starch, gelatin, gum tragacanth, methyl cellulose, hydroxypropylmethyl-cellulose, sodium carboxymethyl cellulose and/or polyvinylpyrrolidone (PVP); etc. can be mentioned. If necessary, disintegrating agents such as cross-linked polyvinylpyrrolidone, agar-agar, alginic acid or its salts like sodium alginate, lubricating agents such as magnesium stearate and binding agents may be added as a carrier.

The oral preparations may include sealed soft capsules that are made from gelatin and plastic agents such as glycol or sorbitol, and hard gelatin capsules that are made from gelatin. The hard gelatin capsules may contain the active compound as a mixture with fillers such as lactose, binding agents such as starch, and/or lubricating agents such as talc or magnesium stearate. In a soft capsule, the active compound may be dissolved or dispersed in a suitable medium such as fatty acid, liquid paraffin or liquid polyethyleneglycol. Furthermore, a stabilizing agent may be included. All formulations for oral administration may contain a suitable amount of the active compound for such administration.

The active compound can also be formulated as an injection preparation, such as, for example, a large pill-type injection or continuous-type injection, for parenteral administration. The injection preparation may be provided in the form of an ampoule having a preservative or a unit dosage form charged in a multi-dose container. The compositions may take such forms as suspensions in oily or liquefied vehicles, solutions or emulsions and may contain such components for formulations as suspending agents, stabilizing agents and/or dispersing agents.

Furthermore, the active ingredient can be a form of dry powder which is intended to be reconstructed by dissolving in a suitable vehicle such as sterilized pyrogen-free water prior to use.

The compounds of the present invention can also be formulated into compositions for rectal administration, such as suppository or retention enema, utilizing typical suppository bases such as cocoa butter or other glycerides.

The pharmaceutical compositions according to the present invention contain the active ingredient in an amount effective to achieve its intended purpose. More specifically, the therapeutically effective amount means the amount of the active compound effective to prolong the survival of the subject to be treated, or to prevent, alleviate or ameliorate the symptoms of the disease. A skilled artisan would be able to determine the therapeutically effective amount, particularly in light of the detailed description provided herein.

When the compound is formulated to a unit dosage form, the active compounds of formula (1) are preferably contained in an amount of about 0.1 to 1,000 mg per unit dosage. The dosage of the compounds of formula (1) depends on the prescription of a physician, taking into account such factors as body weight or age of a patient, specific nature of the disease, severity of the disease, etc. However, dosage needed for the treatment of an adult is typically from about 1 to 1,000 mg per day, depending on the intensity and frequency of the administration. When administered to an adult via intra-muscular or intravenous routes, total dosage typically from about 1 to 500 mg per day will be sufficient when separately administered in a single dosage, but for some patients a higher daily dosage may be desirable.

The present invention further provides a method for the prevention or treatment of diseases associated with human xanthine oxidase, using a therapeutically effective amount of the compounds of formula (1), pharmaceutically acceptable salts or isomers thereof. The "diseases associated with human xanthine oxidase" mean such diseases that can be treated or prevented by inhibiting human xanthine oxidase, and they include but are not limited to hyperuricemia, gout, heart failure, cardiovascular disease, hypertension, diabetes, complications of diabetes, kidney disease, inflammation and articular disease, inflammatory bowel disease, etc. As examples of said complications of diabetes, hyperlipidemia, atherosclerosis, obesity, hypertension, restinosis, renal failure, etc. may be mentioned.

As used herein, "treatment" means the interruption or delay of the progress of the disease when applied to a subject showing the onset of disease symptoms, and "prevention" means the interruption or delay of the sign of the onset of disease when applied to a subject who does not show, but is at risk of, the onset of disease symptoms.

BEST MODE FOR CARRYING OUT THE INVENTION

Figure 1:
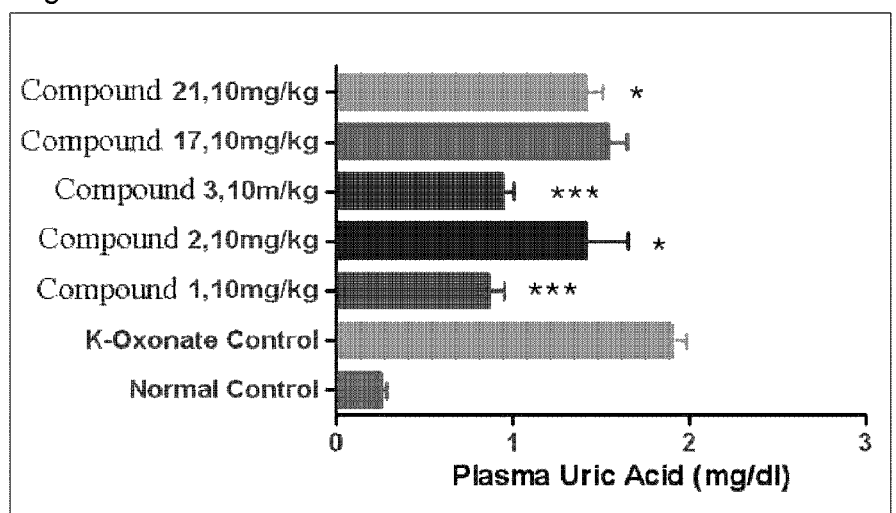
FIG. 1 is a graph showing the result of measuring the uric acid concentration (mg/dl) in the plasma according to the procedure of Experiment 2 (***$P<0.001$, t-test, *$P<0.05$, **$P<0.01$ Dunnett's Multiple Comparison test).

Hereinafter, the present invention will be more specifically explained by preparations, examples and experiments. However, it should be understood that the scope of the present invention is not confined thereto.

Preparation 1: Synthesis of 1-(1H-indol-5-yl)pyrazole-4-carboxylic acid ethyl ester

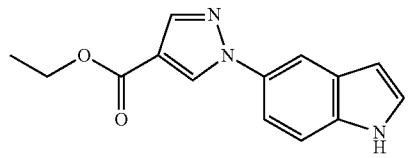 [SMILES: CCOC(=O)c1cnn(-c2ccc3[nH]ccc3c2)c1]

1H-pyrazole-4-carboxylic acid ethyl ester (1.00 g, 7.14 mmol) and 1H-indol-5-ylboronic acid (1.15 g, 7.14 mmol) were dissolved in N,N-dimethylformamide (70 mL). Cupper (II) acetate (0.972 g, 5.35 mmol) and pyridine (1.2 mL, 14.8 mmol) were added, and the mixture was stirred for 3 days at room temperature. The solvent was distilled off under reduced pressure and the residue was purified by column chromatography to give the title compound (1.40 g, 5.47 mmol, 77% Yield).

NMR: $^1$H-NMR (CDCl$_3$) δ 8.39 (1H, s), 8.30 (1H, br), 8.11 (1H, s), 7.92 (1H, d), 7.54 (1H, dd), 7.47 (1H, d), 7.31 (1H, t), 6.64-6.62 (1H, m), 4.35 (2H, q), 1.39 (1H, t)

Mass (EI) 256 (M$^+$+1)

Preparation 2: Synthesis of 1-(3-cyano-1H-indol-5-yl)pyrazole-4-carboxylic acid ethyl ester The title compound was obtained via the following processes (1), (2) and (3).

(1) Synthesis of 1-(3-formyl-1H-indol-5-yl)pyrazole-4-carboxylic acid ethyl ester

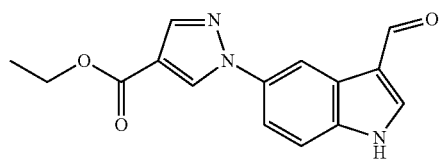 [SMILES: CCOC(=O)c1cnn(-c2ccc3[nH]cc(C=O)c3c2)c1]

Oxalyl chloride (0.56 mL, 6.6 mmol) was added to anhydrous dichloromethane (50 mL), N,N-dimethylformamide (0.51 mL, 6.6 mmol) was added thereto at 0° C., and the mixture was stirred for 30 min at 0° C. To this reaction solution was added a mixture of 1-(1H-indol-5-yl)pyrazole-4-carboxylic acid ethyl ester (1.40 g, 5.47 mmol) obtained in Preparation 1 and dichloromethane (50 mL). The mixture was stirred under reflux for 1 h at room temperature, and the solvent was removed. Tetrahydrofuran (100 mL) and 20% aqueous ammonium acetate solution (100 mL) were added, which was then heated for 30 min while being stirred under reflux. After completion of the reaction, the reaction solution was cooled. Ethyl acetate was added and the mixture was washed with aqueous sodium hydrogen carbonate solution. The organic layer was dried over anhydrous magnesium sulfate and concentrated under reduced pressure to give the title compound.

Mass (EI) 284 (M$^+$+1)

(2) Synthesis of 1-[3-[(E,Z)-hydroxyiminomethyl]-1H-indol-5-yl]pyrazole-4-carboxylic acid ethyl ester

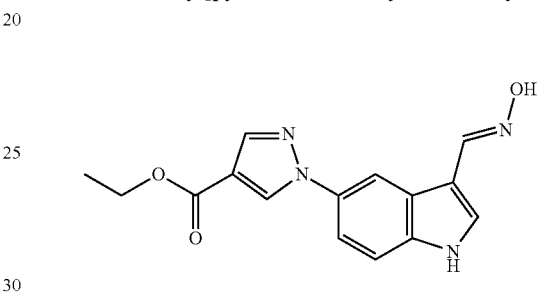

1-(3-Formyl-1H-indol-5-yl)pyrazole-4-carboxylic acid ethyl ester obtained in Process (1) was dissolved in pyridine (150 mL), and hydroxyammoniumchloride (499 mg, 7.18 mmol) was added. The mixture was heated for 5 h while being stirred under reflux. After completion of the reaction, the solvent was removed under reduced pressure. The residue was filtered through silica gel using acetone as a solvent to give the title compound.

Mass (EI) 299 (M$^+$+1)

(3) Synthesis of 1-(3-cyano-1H-indol-5-yl)pyrazole-4-carboxylic acid ethyl ester

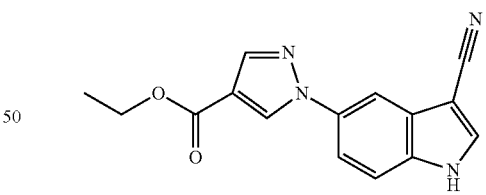

1-[3-[(E,Z)-hydroxyiminomethyl]-1H-indol-5-yl]pyrazole-4-carboxylic acid ethyl ester obtained in Process (2) was dissolved in anhydrous tetrahydrofuran (94 mL), di(imidazol-1-yl)methanthione (90%, 2.79 g, 14.1 mmol) was added, and the mixture was stirred for 2 h at room temperature. After completion of the reaction, the reaction solution was concentrated under reduced pressure and the resulting solid was purified by column chromatography to give the title compound (1.32 g, 4.71 mmol, 86% Yield).

NMR: $^1$H-NMR (DMSO-d$_6$) δ 12.40 (1H, br), 9.20 (1H, s), 8.37 (1H, s), 8.21 (1H, d), 8.14 (1H, s), 7.89 (1H, dd), 7.68 (1H, d), 4.29 (2H, q), 1.32 (3H, t)

Mass (EI) 281 (M$^+$+1)

Preparation 3: Synthesis of 1-(3-cyano-1-isopropyl-indol-5-yl)pyrazole-4-carboxylic acid ethyl ester

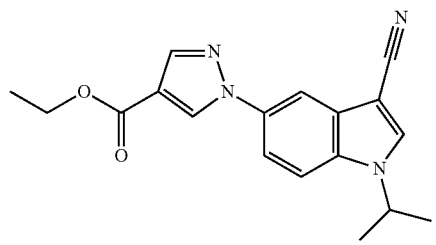 [SMILES: CCOC(=O)c1cnn(-c2ccc3c(c2)c(C#N)cn3C(C)C)c1]

1-(3-Cyano-1H-indol-5-yl)pyrazole-4-carboxylic acid ethyl ester (13.84 g, 49.38 mmol) obtained in Preparation 2 was dissolved in acetonitrile (200 mL). Cesium carbonate (32.17 g, 98.74 mmol) and 2-iodopropane (19.7 mL, 198 mmol) were added, which was then heated for 5 h while being stirred under reflux. After completion of the reaction, the reaction solution was concentrated under reduced pressure and the resulting solid was purified by column chromatography to give the title compound (13.87 g, 43.03 mmol, 87% Yield).

NMR: $^1$H-NMR (CDCl$_3$) δ 8.48 (1H, s), 8.16 (1H, s), 8.06 (1H, d), 7.82 (1H, s), 7.78 (1H, dd), 7.57 (1H, d), 4.80-4.73 (1H, m), 4.38 (2H, q), 1.64 (6H, d), 1.42 (3H, t)

Mass (EI) 323 (M$^+$+1)

Preparation 4: Synthesis of 1-[3-cyano-1-cyclopropyl-indol-5-yl]pyrazole-4-carboxylic acid ethyl ester

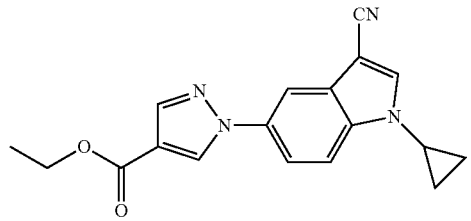 [SMILES: CCOC(=O)c1cnn(-c2ccc3c(c2)c(C#N)cn3C2CC2)c1]

1-(3-Cyano-1H-indol-5-yl)pyrazole-4-carboxylic acid ethyl ester (200 mg, 0.71 mmol) obtained in Preparation 2, cyclopropyl boronic acid (129 mg, 1.42 mmol), copper (II) acetate (136 mg, 0.71 mmol), potassium hexamethyldisilazide (150 mg, 0.71 mmol) and N,N-dimethyl-4-aminopyridine (275 g, 2.13 mmol) were dissolved in toluene (50 mL) and stirred for 15 h at 95° C. Ethyl acetate (50 mL) was added, and the mixture was washed with sodium bicarbonate solution. The organic layer was separated, dried over magnesium sulfate, filtered, and purified by column chromatography to give the title compound (120 mg, 52% Yield).

Mass (EI) 321 (M$^+$+1)

Preparation 5: Synthesis of 1-(3-cyano-1-sec-butyl-indol-5-yl)-pyrazole-4-carboxylic acid ethyl ester

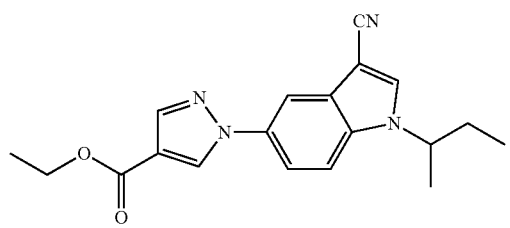 [SMILES: CCOC(=O)c1cnn(-c2ccc3c(c2)c(C#N)cn3C(C)CC)c1]

1-(3-Cyano-1H-indol-5-yl)pyrazole-4-carboxylic acid ethyl ester (100 mg, 0.36 mmol) obtained in Preparation 2 was dissolved in N,N-dimethylformamide, and sodium hydride (21 mg, 0.54 mmol) was added at 0° C. After stirring for 10 min, 2-iodobutane (78 mg, 0.43 mmol) was added, which was then stirred for 2 h. Ethyl acetate (50 mL) was added, and the mixture was washed with aqueous ammonium chloride solution. The organic layer was separated, dried over anhydrous magnesium sulfate, and filtered. The solvent was removed to give the title compound (102 mg, 85% Yield).

Mass (EI): 337 (M+1)

Preparation 6: Synthesis of 1-[3-cyano-1-cyclobutyl-indol-5-yl]pyrazole-4-carboxylic acid ethyl ester

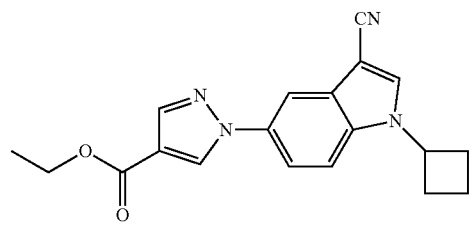 [SMILES: CCOC(=O)c1cnn(-c2ccc3c(c2)c(C#N)cn3C2CCC2)c1]

1-(3-Cyano-1H-indol-5-yl)pyrazole-4-carboxylic acid ethyl ester (100 mg, 0.36 mmol) obtained in Preparation 2, sodium hydride (17 mg, 0.72 mmol) and bromocyclobutane (0.34 mL, 3.6 mmol) were reacted according to the same procedure as Preparation 5 to give the title compound (23 mg, 19% Yield).

Mass (EI) 335 (M$^+$+1)

Preparation 7: Synthesis of 1-(3-cyano-1-cyclopentyl-indol-5-yl)-pyrazole-4-carboxylic acid ethyl ester

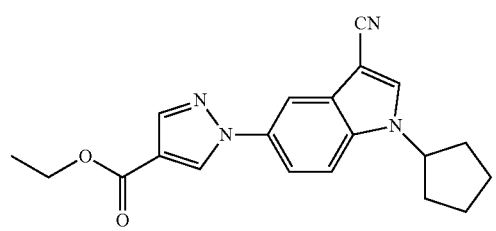 [SMILES: CCOC(=O)c1cnn(-c2ccc3c(c2)c(C#N)cn3C2CCCC2)c1]

1-(3-Cyano-1H-indol-5-yl)pyrazole-4-carboxylic acid ethyl ester (100 mg, 0.36 mmol) obtained in Preparation 2, sodium hydride (21 mg, 0.54 mmol) and bromocyclopentane (60 mg, 0.43 mmol) were reacted according to the same procedure as Preparation 5 to give the title compound (91 mg, 74% Yield).

Mass (EI): 349 (M+1)

Preparation 8: Synthesis of 1-{3-cyano-1-[1-(methacryloxy)propan-2-yl]-indol-5-yl}-pyrazole-4-carboxylic acid ethyl ester

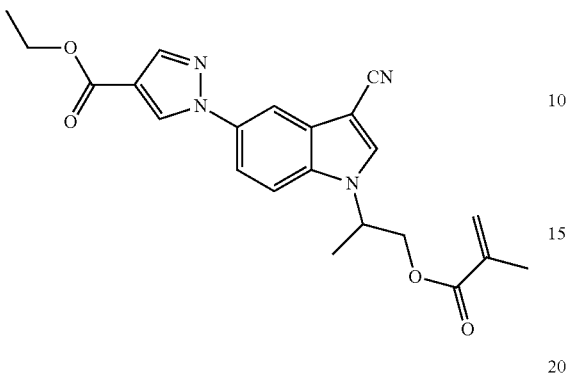

1-(3-Cyano-1H-indol-5-yl)-pyrazole-4-carboxylic acid ethyl ester (300 mg, 0.17 mmol) obtained in Preparation 2, 2-methylsulfonyloxypropyl 2-methylprop-2-enoate (600 mg, 2.6 mmol) and sodium hydride (70 mg, 0.25 mmol) were reacted according to the same procedure as Preparation 5 to give the title compound (200 mg, 0.49 mmol, 46% Yield).

NMR: $^1$H-NMR (CDCl$_3$) (1:1 mixture) δ 8.45 (2H, s), 8.13 (2H, s), 8.04 (2H, m), 7.80 (1H, s), 7.76 (2H, m), 7.66 (1H, s), 7.57 (2H, m), 6.17 (1H, s), 6.13 (1H, m), 6.04 (1H, s), 5.93 (1H, s), 5.63~5.53 (4H, m), 5.34 (1H, m), 5.02 (1H, m), 4.37 (4H, q), 1.88 (3H, s), 1.82 (3H, s), 1.71 (3H), 1.46 (3H, d), 1.39 (6H, t)

Mass (EI) 407 (M$^+$+1)

Preparation 9: Synthesis of 1-[3-cyano-1-(1-hydroxypropan-2-yl)-indol-5-yl]-pyrazole-4-carboxylic acid ethyl ester

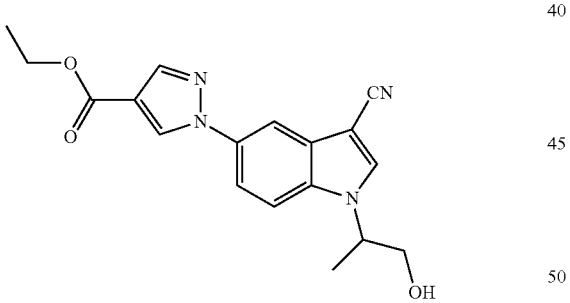

To 1-{3-cyano-1-[1-(methacryloxy)propan-2-yl]-indol-5-yl}-pyrazole-4-carboxylic acid ethyl ester (200 mg, 0.49 mmol) obtained in Preparation 8 were added tetrahydrofuran (8 mL), methanol (8 mL) and 1N-aqueous sodium hydroxide solution (8 mL), which was then stirred for 30 min at room temperature. After completion of the reaction, the reaction solution was concentrated under reduced pressure, and 1N-aqueous hydrochloric acid solution (10 mL) was added. The resulting solid was dried to give 1-[3-cyano-1-(hydroxypropan-2-yl-1H-indol-5-yl)-pyrazole-4-carboxylic acid (87 mg, 0.28 mmol, 57% Yield). This compound was dissolved in N,N-dimethylformamide (5 mL), potassium carbonate (46 mg, 0.33 mmol) and bromoethane (0.06 mL, 0.84 mmol) were added, and the mixture was stirred for 12 h at room temperature. After completion of the reaction, the reaction solution was concentrated under reduced pressure and purified by column chromatography to give the title compound (75 mg, 0.22 mmol, 79% Yield).

NMR: $^1$H-NMR (CDCl$_3$) (1:1 mixture) δ 8.45 (2H, s), 8.13 (2H, s), 8.04 (2H, m), 7.88 (1H, s), 7.78 (1H, s), 7.74 (2H, m), 7.55 (2H, m), 4.35 (4H, q), 4.27 (2H, m), 4.12 (2H, m), 3.97 (2H, m), 1.66 (3H, d), 1.39 (6H, t), 1.31 (3H, d)

Mass (EI) 339 (M$^+$+1)

Preparation 10: Synthesis of 1-[3-cyano-1-(1-fluoropropan-2-yl)-indol-5-yl]-pyrazole-4-carboxylic acid ethyl ester

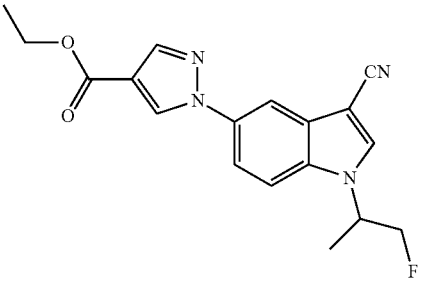 [SMILES: CCOC(=O)c1cnn(-c2ccc3c(c2)c(C#N)cn3C(C)CF)c1]

To 1-[3-cyano-1-(1-hydroxypropan-2-yl)-indol-5-yl]-pyrazole-4-carboxylic acid ethyl ester (75 mg, 0.22 mmol) obtained in Preparation 9 were added dichloromethane (4 mL) and (dimethylamino)sulfur trifluoride (0.04 mL, 0.3 mmol) in the order. The mixture was stirred for 1 h at room temperature, ethyl acetate (20 mL) was added thereto, and the mixture was washed with aqueous sodium chloride solution. The organic layer was separated, dried over anhydrous magnesium sulfate, filtered, and purified by column chromatography to give the title compound (56 mg, 0.16 mmol, 74% Yield).

NMR: $^1$H-NMR (CDCl$_3$) (1:1 mixture) δ 8.45 (2H, s), 8.12 (2H, s), 8.04 (1H, s), 8.03 (1H, s), 7.85 (1H, s), 7.75 (2H, m), 7.73 (1H, s), 7.51 (2H, m), 5.01~4.62 (4H, m), 4.35 (4H, q), 4.46~4.26 (2H, m), 1.70 (3H, dd), 1.45 (3H, d), 1.39 (6H, t)

Mass (EI) 341 (M$^+$+1)

Preparation 11: Synthesis of 1-(3-cyano-1-tetrahydrofuran-3-yl-indol-5-yl)-pyrazole-4-carboxylic acid ethyl ester

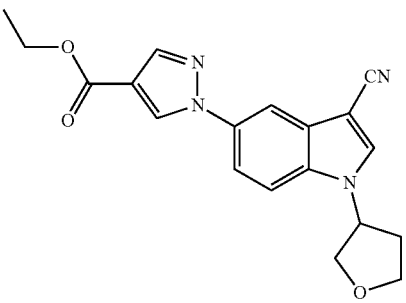 [SMILES: CCOC(=O)c1cnn(-c2ccc3c(c2)c(C#N)cn3C2CCOC2)c1]

1-(3-Cyano-1H-indol-5-yl)-pyrazole-4-carboxylic acid ethyl ester (150 mg, 0.53 mmol) obtained in Preparation 2 and tetrahydrofuran-3-yl-methanesulfonate (270 mg, 1.59 mmol)

were reacted according to the same procedure as Preparation 5 to give the title compound (150 mg, 0.43 mmol, 80% Yield).

NMR: ¹H-NMR (CDCl₃) δ 8.45 (1H, s), 8.13 (1H, m), 8.04 (1H, d), 7.85 (1H, s), 7.78 (1H, dd), 7.59 (1H, d), 5.13 (1H, m), 4.36 (2H, q), 4.21 (2H, m), 4.24~4.18 (1H, m), 4.10~3.95 (1H, m), 2.63 (1H, m), 2.20 (1H, m), 1.39 (1H, t)

Mass (EI) 351 (M⁺+1)

Preparation 12: Synthesis of 1-(1H-indol-5-yl)-3-methyl-pyrazole-4-carboxylic acid ethyl ester

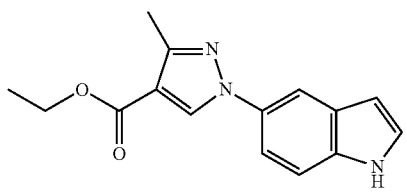 [SMILES: CCOC(=O)c1cn(-c2ccc3[nH]ccc3c2)nc1C]

3-Methyl-1H-pyrazole-4-carboxylic acid ethyl ester (1.43 g, 9.27 mmol) and 1H-indol-5-ylboronic acid (1.50 g, 9.29 mmol) were dissolved in N,N-dimethylformamide (93 mL). Cupper (II) acetate (1.27 g, 6.98 mmol) and pyridine (1.50 mL, 18.5 mmol) were added, and the mixture was stirred for 3 days at room temperature. The solvent was distilled off under reduced pressure, and the residue was purified by column chromatography to give the title compound (1.2433 g, 4.62 mmol, 50% Yield).

NMR: ¹H-NMR (CDCl₃) δ 8.35 (1H, s), 8.30 (1H, br), 7.91 (1H, d), 7.53 (1H, dd), 7.47 (1H, d), 7.32 (1H, t), 6.63 (1H, s), 4.35 (2H, q), 2.61 (3H, s), 1.41 (3H, t)

Mass (EI) 270 (M⁺+1)

Preparation 13: Synthesis of 1-(3-cyano-1H-indol-5-yl)-3-methyl-pyrazole-4-carboxylic acid ethyl ester The title compound was obtained via the following processes (1), (2) and (3).

(1) Synthesis of 1-(3-formyl-1H-indol-5-yl)-3-methyl-pyrazole-4-carboxylic acid ethyl ester

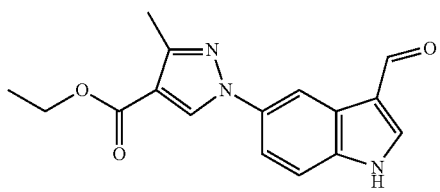 [SMILES: CCOC(=O)c1cn(-c2ccc3[nH]cc(C=O)c3c2)nc1C]

1-(1H-indol-5-yl)-3-methyl-pyrazole-4-carboxylic acid ethyl ester (540 mg, 2.01 mmol) obtained in Preparation 12, oxalyl chloride (0.20 mL, 2.36 mmol), N,N-dimethylformamide (0.19 mL, 2.45 mmol) and dichloromethane were reacted according to the same procedure as Process (1) of Preparation 2 to give the title compound.

Mass (EI) 298 (M⁺+1)

(2) Synthesis of 1-[3-[(E,Z)-hydroxyhninomethyl]-1H-indol-5-yl]-3-methyl-pyrazole-4-carboxylic acid ethyl ester

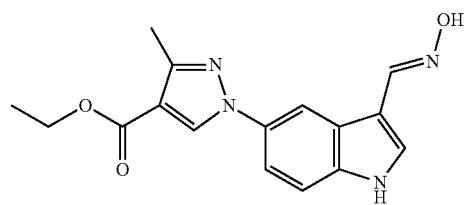

1-(3-Formyl-1H-indol-5-yl)-3-methyl-pyrazole-4-carboxylic acid ethyl ester obtained in Process (1), hydroxyammonium chloride (172 mg, 2.47 mmol) and pyridine were reacted according to the same procedure as Process (2) of Preparation 2 to give the title compound.

Mass (EI) 313 (M⁺+1)

(3) Synthesis of 1-(3-cyano-1H-indol-5-yl)-3-methyl-pyrazole-4-carboxylic acid ethyl ester

1-[3-[(E,Z)-hydroxyiminomethyl]-1H-indol-5-yl]-3-methyl-pyrazole-4-carboxylic acid ethyl ester obtained in Process (2), di(imidazol-1-yl)methanthione (90%, 1.05 g, 5.31 mmol) and anhydrous tetrahydrofuran were reacted according to the same procedure as Process (3) of Preparation 2 to give the title compound (420.1 mg, 1.43 mmol, 71% Yield).

NMR: ¹H-NMR (CDCl₃) δ 12.40 (1H, br), 9.06 (1H, s), 8.35 (1H, s), 8.16 (1H, d), 7.86 (1H, dd), 7.65 (1H, d), 4.27 (2H, q), 2.47 (3H, s), 1.32 (3H, t)

Mass (EI) 295 (M⁺+1)

Preparation 14: Synthesis of 1-[3-cyano-1-isopropyl-indol-5-yl]-3-methyl-pyrazole-4-carboxylic acid ethyl ester

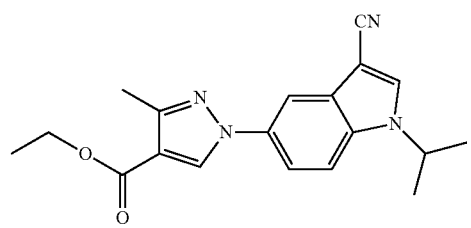 [SMILES: CCOC(=O)c1cn(-c2ccc3c(c2)c(C#N)cn3C(C)C)nc1C]

1-(3-Cyano-1H-indol-5-yl)-3-methyl-pyrazole-4-carboxylic acid ethyl ester (140 mg, 0.48 mmol) obtained in Preparation 13, sodium hydride (17 mg, 0.71 mmol) and 2-iodopropane (0.10 mL, 0.96 mmol) were reacted according to the same procedure as Preparation 5 to give the title compound (150 mg, 93% Yield).

Preparation 15: Synthesis of 1-(1H-indol-5-yl)-3-(trifluoromethyl)pyrazole-4-carboxylic acid ethyl ester

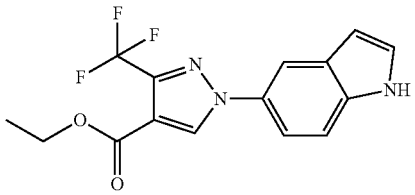 [SMILES: CCOC(=O)c1cn(-c2ccc3[nH]ccc3c2)nc1C(F)(F)F]

1H-indol-5-ylboronic acid (1,000 mg, 6.21 mmol) and 3-trifluoromethyl-1H-pyrazole-4-carboxylic acid ethyl ester (646 mg, 3.10 mmol) were reacted according to the same procedure as Preparation 1 to give the title compound (723 mg, 72% Yield).
NMR: $^1$H-NMR (CDCl$_3$) 8.46 (1H, s), 7.93 (1H, s), 7.53 (1H, d), 7.51 (1H, d), 7.33 (1H, d), 6.64 (1H, d), 4.36 (2H, q), 1.37 (3H, t)
Mass (EI) 324 (M$^+$+1)

Preparation 16: Synthesis of 1-(3-formyl-1H-indol-5-yl)-3-(trifluoromethyl)pyrazole-4-carboxylic acid ethyl ester

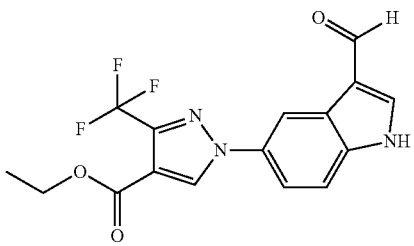 [SMILES: CCOC(=O)c1cn(-c2ccc3[nH]cc(C=O)c3c2)nc1C(F)(F)F]

1-(1H-indol-5-yl)-3-(trifluoromethyl)pyrazole-4-carboxylic acid ethyl ester (720 mg, 2.23 mmol) obtained in Preparation 15 was reacted according to the same procedure as Process (1) of Preparation 2 to give the title compound (750 mg, 96% Yield).
Mass (EI) 352 (M$^+$+1)

Preparation 17: Synthesis of 1-[3-[(E,Z)-hydroxyiminomethyl]-1H-indol-5-yl]-3-(trifluoromethyl)pyrazole-4-carboxylic acid ethyl ester

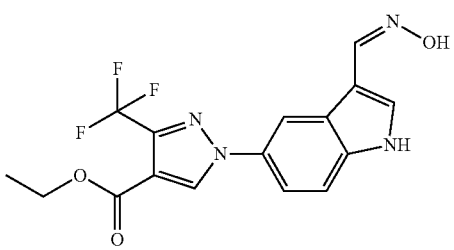 [SMILES: CCOC(=O)c1cn(-c2ccc3[nH]cc(/C=N\O)c3c2)nc1C(F)(F)F]

1-(3-Formyl-1H-indol-5-yl)-3-(trifluoromethyl)pyrazole-4-carboxylic acid ethyl ester (750 mg, 2.13 mmol) obtained in Preparation 16 was reacted according to the same procedure as Process (2) of Preparation 2 to give the title compound (680 mg, 87% Yield).
Mass (EI) 367 (M$^+$+1)

Preparation 18: Synthesis of 1-(3-cyano-1H-indol-5-yl)-3-(trifluoromethyl)pyrazole-4-carboxylic acid ethyl ester

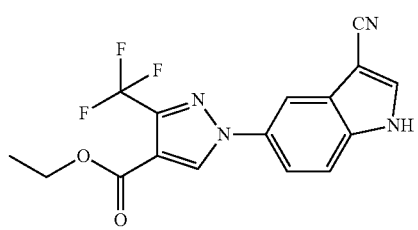 [SMILES: CCOC(=O)c1cn(-c2ccc3[nH]cc(C#N)c3c2)nc1C(F)(F)F]

1-{3-[(E,Z)-hydroxyiminomethyl]-1H-indol-5-yl}-3-(trifluoromethyl)pyrazole-4-carboxylic acid ethyl ester (680 mg, 1.86 mmol) obtained in Preparation 17 was reacted according to the same procedure as Process (3) of Preparation 2 to give the title compound (562 mg, 87% Yield).
Mass (EI) 349 (M$^+$+1)

Preparation 19: Synthesis of 1-[3-cyano-1-isopropyl-indol-5-yl]-3-(trifluoromethyl)pyrazole-4-carboxylic acid ethyl ester

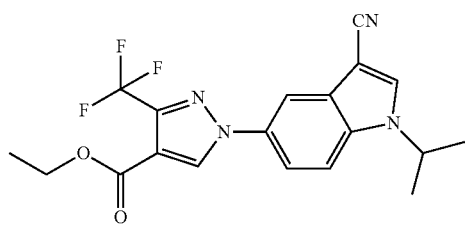 [SMILES: CCOC(=O)c1cn(-c2ccc3c(c2)c(C#N)cn3C(C)C)nc1C(F)(F)F]

1-(3-Cyano-1H-indol-5-yl)-3-(trifluoromethyl)pyrazole-4-carboxylic acid ethyl ester (130 mg, 0.37 mmol) obtained in Preparation 18, sodium hydride (13 mg, 0.56 mmol) and 2-iodopropane (0.07 mL, 0.74 mmol) were reacted according to the same procedure as Preparation 5 to give the title compound (130 mg, 90% Yield).
Mass (EI) 391 (M$^+$+1)

Preparation 20: Synthesis of 1-[3-cyano-1-(cyclopropylmethyl)indol-5-yl]-3-(trifluoromethyl)pyrazole-4-carboxylic acid ethyl ester

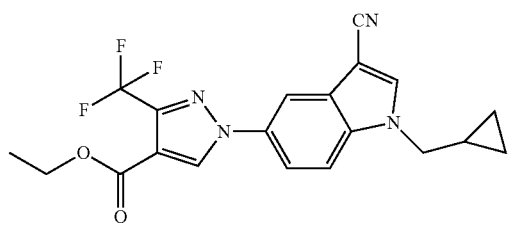 [SMILES: CCOC(=O)c1cn(-c2ccc3c(c2)c(C#N)cn3CC2CC2)nc1C(F)(F)F]

1-(3-Cyano-1H-indol-5-yl)-3-(trifluoromethyl)pyrazole-4-carboxylic acid ethyl ester (110 mg, 0.32 mmol) obtained in Preparation 18, sodium hydride (11 mg, 0.47 mmol) and bromomethylcyclopropane (0.06 mL, 0.64 mmol) were reacted according to the same procedure as Preparation 5 to give the title compound (110 mg, 85% Yield).

Mass (EI) 403 (M⁺+1)

Preparation 21: Synthesis of 1-(3-nitro-1H-indol-5-yl)pyrazole-4-carboxylic acid ethyl ester

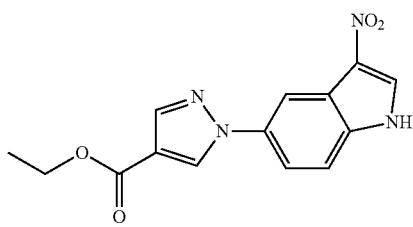 [SMILES: CCOC(=O)c1cnn(-c2ccc3[nH]cc([N+](=O)[O-])c3c2)c1]

1-(1H-indol-5-yl)pyrazole-4-carboxylic acid ethyl ester (293.6 mg, 1.15 mmol) obtained in Preparation 1 was dissolved in acetonitrile (2.3 mL). Silver nitrate (214.9 mg, 1.27 mmol) was added at 0° C., and benzoyl chloride was slowly added in drops under nitrogen atmosphere. After completion of the reaction, the reaction solution was cooled, ethyl acetate was added, which was then washed with aqueous sodium hydrogen carbonate solution. The organic layer was dried over anhydrous magnesium sulfate and concentrated under reduced pressure. The resulting solid was purified by column chromatography to give the title compound (119.1 mg, 0.397 mmol, 34% Yield).

Mass (EI) 301 (M⁺+1)

Preparation 22: Synthesis of 1-(1-isopropyl-3-nitro-indol-5-yl)pyrazole-4-carboxylic acid ethyl ester

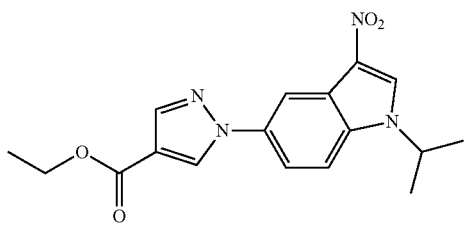 [SMILES: CCOC(=O)c1cnn(-c2ccc3c(c2)c([N+](=O)[O-])cn3C(C)C)c1]

1-(3-Nitro-1H-indol-5-yl)pyrazole-4-carboxylic acid ethyl ester (119.1 mg, 0.397 mmol) obtained in Preparation 21 was dissolved in N,N-dimethylformamide (4.0 mL). Sodium hydride (55%, 26.0 mg, 0.60 mmol) was added at 0° C., and the mixture was stirred for 10 min at room temperature. 2-Iodopropane (19.7 mL, 198 mmol) was added, and stirred for 15 h at room temperature. The solvent was distilled off, ethyl acetate was added to the residue, and the mixture was washed with aqueous ammonium chloride solution. The organic layer was separated, dried over anhydrous magnesium sulfate, filtered, and purified by column chromatography to give the title compound (60.8 mg, 0.178 mmol, 45% Yield).

Mass (EI) 343 (M⁺+1)

Preparation 23: Synthesis of 1-(1H-indol-5-yl)-1,2,4-triazole-3-carboxylic acid methyl ester

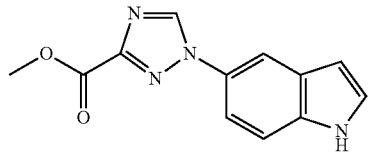 [SMILES: COC(=O)c1ncn(-c2ccc3[nH]ccc3c2)n1]

1H-1,2,4-triazole-3-carboxylic acid methyl ester (1.12 g, 8.79 mmol), 1H-indol-5-ylboronic acid (1.42 g, 8.79 mmol), N,N-dimethylformamide (90 mL), copper (II) acetate (1.20 g, 6.60 mmol) and pyridine (1.40 mL, 17.3 mmol) were reacted according to the same procedure as Preparation 1 to give the title compound (519.7 mg, 2.15 mmol, 24% Yield).

NMR: ¹H-NMR (CDCl₃) δ 8.52 (1H, s), 8.33 (1H, br), 7.88 (1H, s), 7.47-7.42 (2H, m), 7.28 (1H, t), 6.58 (1H, t), 3.98 (3H, s)

Mass (EI) 243 (M⁺+1)

Preparation 24: Synthesis of 1-(1-isopropylindol-5-yl)-1,2,4-triazole-3-carboxylic acid methyl ester

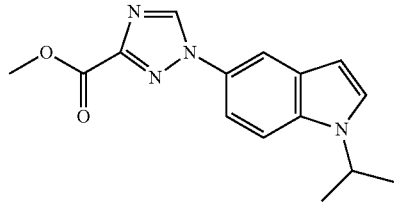 [SMILES: COC(=O)c1ncn(-c2ccc3c(ccn3C(C)C)c2)n1]

1-(1H-indol-5-yl)-1,2,4-triazole-3-carboxylic acid methyl ester (139.5 mg, 0.58 mmol) obtained in Preparation 23, sodium hydride (55%, 38 mg, 0.87 mmol), 2-iodopropane (0.09 mL, 0.90 mmol) and N,N-dimethylformamide (5.8 mL) were reacted according to the same procedure as Preparation 5 to give the title compound (83.4 mg, 0.29 mmol, 51% Yield).

Mass (EI) 285 (M⁺+1)

Preparation 25: Synthesis of 1-(3-cyano-1-isopropyl-indol-5-yl)-1,2,4-triazole-3-carboxylic acid methyl ester The title compound was obtained via the following Processes (1), (2), (3).

(1) Synthesis of 1-(3-formyl-1-isopropyl-indol-5-yl)-1,2,4-triazole-3-carboxylic acid methyl ester

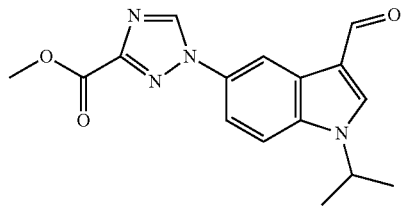 [SMILES: COC(=O)c1ncn(-c2ccc3c(c2)c(C=O)cn3C(C)C)n1]

1-(1-Isopropylindol-5-yl)-1,2,4-triazole-3-carboxylic acid methyl ester (83.4 mg, 0.29 mmol) obtained in Preparation 24, oxalyl chloride (0.03 mL, 0.35 mmol), N,N-dimethylformamide (0.03 mL, 0.39 mmol) and dichloromethane were reacted according to the same procedure as Process (1) of Preparation 2 to give the title compound.

Mass (EI) 313 (M⁺+1)

(2) Synthesis of 1-[3-[(E,Z)-hydroxyiminomethyl]-1-isopropyl-indol-5-yl]-1,2,4-triazole-3-carboxylic acid methyl ester

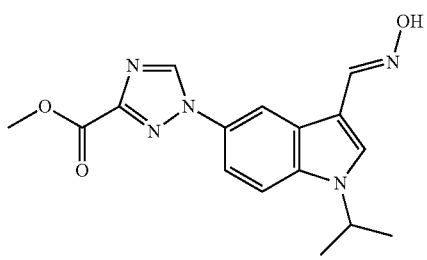 [SMILES: COC(=O)c1ncn(-c2ccc3c(c2)c(/C=N/O)cn3C(C)C)n1]

1-(3-Formyl-1-isopropyl-indol-5-yl)-1,2,4-triazole-3-carboxylic acid methyl ester obtained in Process (1), hydroxyammonium chloride (24 mg, 0.35 mmol) and pyridine were reacted according to the same procedure as Process (2) of Preparation 2 to give the title compound.

Mass (EI) 328 (M⁺+1)

(3) Synthesis of 1-(3-cyano-1-isopropyl-indol-5-yl)-1,2,4-triazole-3-carboxylic acid methyl ester

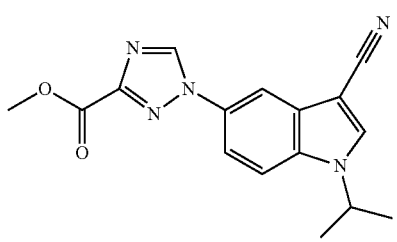 [SMILES: COC(=O)c1ncn(-c2ccc3c(c2)c(C#N)cn3C(C)C)n1]

1-[3-[(E,Z)-hydroxyiminomethyl]-1-isopropyl-indol-5-yl]-1,2,4-triazole-3-carboxylic acid methyl ester obtained in Process (2), di(imidazol-1-yl)methanthione (90%, 148 mg, 0.75 mmol) and anhydrous tetrahydrofuran were reacted according to the same procedure as Process (3) of Preparation 2 to give the title compound.

Mass (EI) 310 (M⁺+1)

Preparation 26: Synthesis of 1-(1H-indol-5-yl)-imidazole-4-carboxylic acid ethyl ester

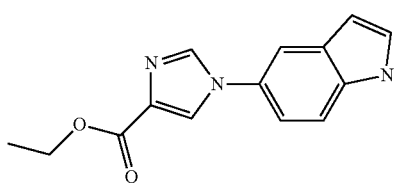 [SMILES: CCOC(=O)c1cn(-c2ccc3[nH]ccc3c2)cn1]

A mixture of ethylcyanoacetate (1.0 g, 7.75 mmol) and t-butoxy bis(dimethylamino)methane (2.7 g, 15.5 mmol) was stirred for 18 h at room temperature. After distillation under reduced pressure, 5-aminoindole (1.3 g, 7.75 mmol) was added. The mixture was dissolved in n-butanol, and refluxed for 15 h. The reaction solution was cooled, ethyl acetate was added thereto, and washed with aqueous sodium bicarbonate solution. The organic layer was dried over anhydrous magnesium sulfate and concentrated under reduced pressure. The resulting solid was filtered, washed with ethyl acetate and dried to give the title compound (0.33 g, 17% Yield).

NMR: ¹H-NMR (CDCl₃) δ 8.52 (1H, s), 8.00 (1H, s), 7.88 (1H, s), 7.70 (1H, d), 7.55 (1H, d), 7.40 (1H, d), 7.26 (1H, d), 6.67 (1H, s), 4.48 (2H, q), 1.46 (3H, t)

Mass (EI): 256 (M+1)

Preparation 27: Synthesis of 1-(1-isopropylindol-5-yl)-imidazole-4-carboxylic acid ethyl ester

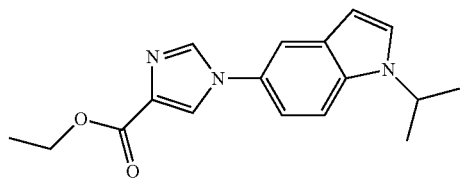 [SMILES: CCOC(=O)c1cn(-c2ccc3c(ccn3C(C)C)c2)cn1]

1-(1H-indol-5-yl)-imidazole-4-carboxylic acid ethyl ester (0.33 g, 1.29 mmol) obtained in Preparation 26, cesium carbonate (0.63 g, 1.94 mmol) and 2-iodopropane (0.26 g, 1.55 mmol) were dissolved in acetonitrile (30 mL) and refluxed for 5 h. Ethyl acetate (50 mL) was added, and the mixture was washed with aqueous sodium bicarbonate solution. The organic layer was separated, dried over anhydrous magnesium sulfate, filtered and purified by column chromatography to give the title compound (90 mg, 24% Yield).

NMR: ¹H-NMR (CDCl₃) δ 8.00 (1H, s), 7.87 (1H, s), 7.67 (1H, s), 7.51 (1H, d), 7.40 (1H, d), 7.26 (1H, d), 6.63 (1H, s), 4.78 (1H, m), 4.48 (2H, q), 1.62 (6H, d), 1.46 (3H, t)

Mass (EI): 298 (M+1)

Preparation 28: Synthesis of 1-(3-formyl-1-isopropyl-indol-5-yl)imidazole-4-carboxylic acid ethyl ester

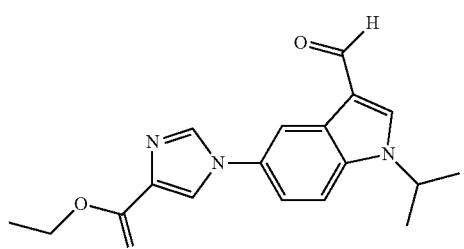

To anhydrous dichloromethane (30 mL) was added oxalyl chloride (0.03 mL, 0.36 mmol). N,N-dimethylformamide (0.03 mL, 0.36 mmol) was added at 0° C., which was then stirred for 30 min at 0° C. To this solution was added 1-(1-isopropylindol-5-yl)-imidazole-4-carboxylic acid ethyl ester (0.09 g, 0.3 mmol) obtained in Preparation 27, and the mixture was stirred for 1 h at room temperature. The solvent was removed, tetrahydrofuran (30 mL) and 20% aqueous ammonium acetate solution (30 mL) were added to the residue, and the mixture was heated for 30 min while being stirred under reflux. The reaction solution was cooled, ethyl acetate was added, and washed with aqueous sodium bicarbonate solution. The organic layer was dried over anhydrous magnesium sulfate and concentrated under reduced pressure. The resulting solid was filtered, washed with ethyl acetate and dried to give the title compound (0.09 g, 92% Yield).

NMR: $^1$H-NMR (CDCl$_3$) δ 10.08 (1H, s), 8.45 (1H, s), 8.06 (1H, s), 8.00 (1H, s), 7.96 (1H, d), 7.59 (1H, d), 7.42 (1H, d), 4.80 (1H, m), 4.48 (2H, q), 1.66 (6H, d), 1.46 (3H, t)

Mass (EI): 326 (M+1)

Preparation 29: Synthesis of 1-[3-[(E,Z)-hydroxyhni-nomethyl]-1-isopropyl-indol-5-yl]imidazole-4-carboxylic acid ethyl ester

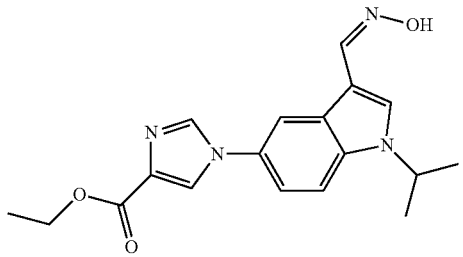 [SMILES: CCOC(=O)c1cn(-c2ccc3c(c2)c(/C=N\O)cn3C(C)C)cn1]

1-(3-Formyl-1-isopropyl-indol-5-yl)imidazole-4-carboxylic acid ethyl ester (0.09 g, 0.27 mmol) obtained in Preparation 28 was dissolved in pyridine (30 mL). After hydroxyammonium chloride (23 mg, 0.33 mmol) was added, the mixture was heated for 5 h while being stirred under reflux. After completion of the reaction, the solvent was concentrated under reduced pressure, ethyl acetate was added to the residue, and the mixture was washed with 1N-aqueous hydrochloric acid solution. The organic layer was dried over anhydrous magnesium sulfate and concentrated under reduced pressure. The resulting solid was washed with ethyl acetate and dried to give the title compound (0.08 g, 98% Yield).

Mass (EI): 341 (M+1)

Preparation 30: Synthesis of 1-(3-cyano-1-isopropyl-indol-5-yl)imidazole-4-carboxylic acid ethyl ester

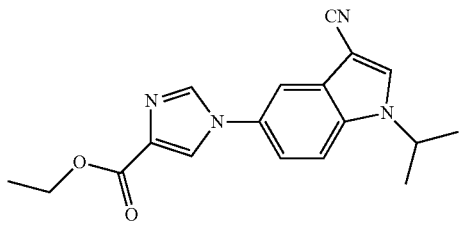 [SMILES: CCOC(=O)c1cn(-c2ccc3c(c2)c(C#N)cn3C(C)C)cn1]

1-[3-[(E,Z)-hydroxyiminomethyl]-1-isopropyl-indol-5-yl]imidazole-4-carboxylic acid ethyl ester (0.08 g, 0.27 mmol) obtained in Preparation 29 was dissolved in anhydrous tetrahydrofuran (30 mL). Di(imidazol-1-yl)methanthione (0.12 g, 0.67 mmol) was added, and stirred for 13 h at room temperature. After completion of the reaction, the reaction solution was concentrated under reduced pressure, ethyl acetate was added, and washed with 0.5N-aqueous hydrochloric acid solution. The organic layer was dried over anhydrous magnesium sulfate and concentrated under reduced pressure. The resulting solid was washed with ethyl acetate and dried to give the title compound (86 mg, 78% Yield).

NMR: $^1$H-NMR (CDCl$_3$) δ 8.04 (2H, d), 7.88 (1H, s), 7.82 (1H, s), 7.63 (1H, d), 7.42 (1H, d), 4.80 (1H, m), 4.43 (2H, q), 1.63 (6H, d), 1.28 (3H, t)

Mass (EI): 323 (M+1)

Preparation 31: Synthesis of 5-(1H-indol-5-yl)-thiophene-2-carboxylic acid methyl ester

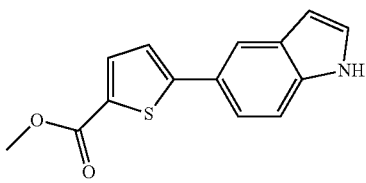 [SMILES: COC(=O)c1ccc(-c2ccc3[nH]ccc3c2)s1]

5-Bromothiophene-2-carboxylic acid methyl ester (0.5 g, 2.26 mmol), 1H-indol-5-ylboronic acid (0.36 g, 2.26 mmol), tetrakis(triphenylphosphine)palladium(0) (0.13 g, 0.11 mmol) and sodium carbonate (0.48 g, 4.52 mmol) were dissolved in dioxane (30 mL) and refluxed for 5 h. Ethyl acetate (30 mL) was added, and the mixture was washed with sodium bicarbonate solution. The organic layer was separated, dried over anhydrous magnesium sulfate, filtered and purified by column chromatography to give the title compound (0.36 g, 62% Yield).

NMR: $^1$H-NMR (CDCl$_3$) δ 8.29 (1H, s), 7.98 (1H, s), 7.81 (1H, s), 7.54 (1H, d), 7.47 (1H, d), 7.31 (2H, s), 6.65 (1H, s), 3.95 (3H, s)

Mass (EI): 257 (M+1)

Preparation 32: Synthesis of 5-(1-isopropylindol-5-yl)-thiophene-2-carboxylic acid methyl ester

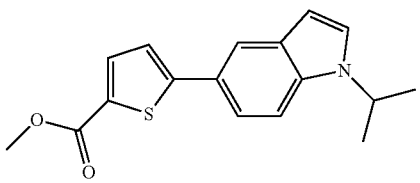 [SMILES: COC(=O)c1ccc(-c2ccc3c(ccn3C(C)C)c2)s1]

5-(1H-indol-5-yl)-thiophene-2-carboxylic acid methyl ester (0.26 g, 1.01 mmol) obtained in Preparation 31, cesium carbonate (0.32 g, 2.02 mmol) and 2-iodopropane (0.25 g, 0.59 mmol) were dissolved in acetonitrile (30 mL) and refluxed for 5 h. Ethyl acetate (50 mL) was added, and the mixture was washed with sodium bicarbonate solution. The organic layer was separated, dried over anhydrous magnesium sulfate, filtered and purified by column chromatography to give the title compound (0.3 g, 99% Yield).

NMR: $^1$H-NMR (CDCl$_3$) δ 7.96 (1H, s), 7.81 (1H, s), 7.54 (1H, d), 7.42 (1H, d), 7.30 (2H, s), 6.60 (1H, s), 3.94 (3H, s)

Mass (EI): 300 (M+1)

Preparation 33: Synthesis of 5-(3-formyl-1-isopropyl-indol-5-yl)-thiophene-2-carboxylic acid methyl ester

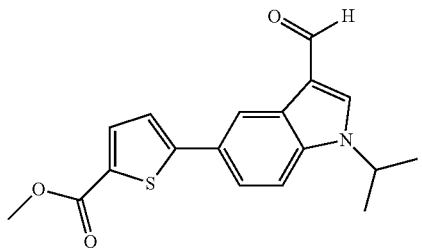 [SMILES: COC(=O)c1ccc(-c2ccc3c(c2)c(C=O)cn3C(C)C)s1]

To anhydrous dichloromethane (30 mL) was added oxalyl chloride (0.1 mL, 1.2 mmol). N,N-dimethylformamide (0.1 mL, 1.2 mmol) was added at 0° C., and stirred for 30 min at 0° C. To this reaction solution was added 5-(1-isopropyl-indol-5-yl)thiophene-2-carboxylic acid methyl ester (0.3 g, 1.0 mmol) obtained in Preparation 32, which was then stirred for 1 h at room temperature. The solvent was removed, tetrahydrofuran (30 mL) and 20% aqueous ammonium acetate solution (30 mL) were added to the residue, and the mixture was heated for 30 min while being stirred under reflux. The reaction solution was cooled, ethyl acetate was added, and the mixture was washed with aqueous sodium bicarbonate solution. The organic layer was dried over anhydrous magnesium sulfate and concentrated under reduced pressure. The resulting solid was filtered, washed with ethyl acetate and dried to give the title compound (0.32 g, 99% Yield).

NMR: $^1$H-NMR (CDCl$_3$) δ 10.08 (1H, s), 8.67 (1H, s), 7.92 (1H, s), 7.84 (1H, d), 7.67 (1H, d), 7.50 (1H, d), 7.42 (1H, d), 4.77 (1H, m), 3.96 (3H, s), 1.68 (6H, d)

Mass (EI): 328 (M+1)

Preparation 34: Synthesis of 5-[3-[(E,Z)-hydroxyiminomethyl]-1-isopropyl-indol-5-yl]-thiophene-2-carboxylic acid methyl ester

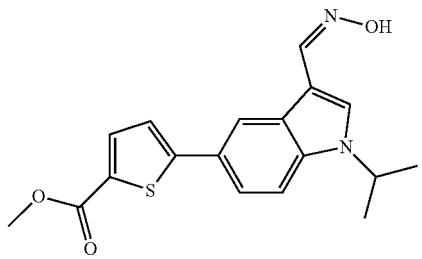 [SMILES: COC(=O)c1ccc(-c2ccc3c(c2)c(/C=N\O)cn3C(C)C)s1]

5-(3-Formyl-1-isopropyl-indol-5-yl)-thiophene-2-carboxylic acid methyl ester (0.32 g, 0.97 mmol) obtained in Preparation 33 was dissolved in pyridine (30 mL), hydroxyammonium chloride (81 mg, 1.17 mmol) was added, and the mixture was heated for 5 h while being stirred under reflux. After completion of the reaction, the solvent was concentrated under reduced pressure, ethyl acetate was added, and the mixture was washed with 1N-aqueous hydrochloric acid solution. The organic layer was dried over anhydrous magnesium sulfate and concentrated under reduced pressure. The resulting solid was washed with ethyl acetate and dried to give the title compound (0.29 g, 89% Yield).

Mass (EI): 343 (M+1)

Preparation 35: Synthesis of 5-(3-cyano-1-isopropyl-indol-5-yl)-thiophene-2-carboxylic acid methyl ester

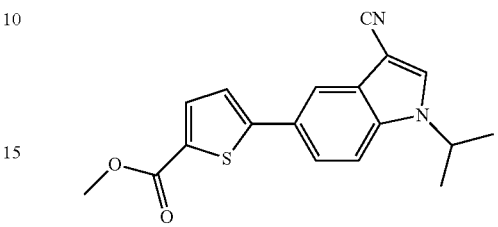

5-[3-[(E,Z)-hydroxyiminomethyl]-1-isopropyl-indol-5-yl]-thiophene-2-carboxylic acid methyl ester (0.29 g, 0.85 mmol) obtained in Preparation 34 was dissolved in anhydrous tetrahydrofuran (30 mL). 2-Chloro-1-methylpyridinium iodide (0.25 g, 1.02 mmol) was added and stirred for 10 min at room temperature. To this reaction solution was slowly added in drops triethylamine (0.47 mL, 3.4 mmol) for 15 min, which was then stirred for 20 h at room temperature. After completion of the reaction, the reaction solution was concentrated under reduced pressure and ethyl acetate was added. The mixture was washed with 0.5N-aqueous hydrochloric acid solution. The organic layer was dried over anhydrous magnesium sulfate and concentrated under reduced pressure. The resulting solid was washed with ethyl acetate and dried to give the title compound (0.183 g, 67% Yield).

NMR: $^1$H-NMR (CD$_3$OD) δ 8.21 (1H, s), 7.96 (1H, s), 7.80 (1H, d), 7.71 (2H, d), 7.49 (1H, d), 4.91 (1H, m), 3.93 (3H, s), 1.61 (6H, d)

Mass (EI): 325 (M+1)

Preparation 36: Synthesis of 2-(1H-indol-5-yl)isonicotinic acid methyl ester

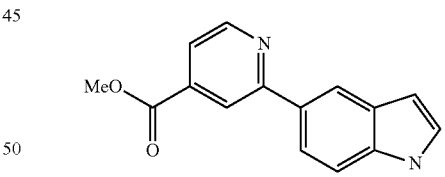

2-Chloroisonicotinic acid methyl ester (1.22 g, 7.11 mmol), 1H-indole-5-boronic acid (1.15 g, 7.13 mmol), 2M-aqueous sodium carbonate solution (10 mL, 20 mmol) and tetrakis(triphenylphosphine)palladium (0.41 g, 0.35 mmol) were dissolved in toluene (140 mL), and stirred for 12 h under reflux. After completion of the reaction, ethyl acetate (200 mL) was added, and washed with aqueous sodium chloride solution. The organic layer was separated, dried over anhydrous magnesium sulfate, concentrated under reduced pressure and purified by column chromatography to give the title compound (440 mg, 1.74 mmol, 25% Yield).

NMR: $^1$H-NMR (CDCl$_3$) δ 8.82 (1H, dd), 8.36 (2H, s), 8.24 (1H, br), 7.95 (1H, dd), 7.71 (1H, dd), 7.51 (1H, d), 7.27 (1H, m), 6.66 (1H, m), 4.00 (3H, s)

Mass (EI) 253 (M$^+$+1)

Preparation 37: Synthesis of 2-(3-cyano-1H-indol-5-yl)isonicotinic acid methyl ester

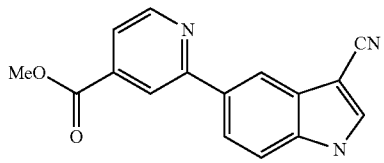 [SMILES: COC(=O)c1ccnc(-c2ccc3[nH]cc(C#N)c3c2)c1]

To anhydrous dichloromethane (35 mL) was added oxalyl chloride (0.23 mL, 2.71 mmol). N,N-dimethylformamide (0.27 mL, 3.48 mmol) was added at 0° C., and the mixture was stirred for 30 min at 0° C. To this reaction solution was added 2-(1H-indol-5-yl)isonicotinic acid methyl ester (0.44 g, 1.74 mmol) obtained in Preparation 36, which was then stirred for 1 h at room temperature. The solvent was removed, tetrahydrofuran (40 mL) and 20% aqueous ammonium acetate solution (30 mL) were added, and the mixture was heated for 30 min while being stirred under reflux. The reaction solution was cooled, ethyl acetate was added, and washed with aqueous sodium bicarbonate solution. The organic layer was separated, dried over anhydrous magnesium sulfate and concentrated under reduced pressure. The resulting solid was filtered, washed with ethyl acetate and dried to give 2-(3-formyl-1H-indol-5-yl)isonicotinic acid methyl ester.

2-(3-Formyl-1H-indol-5-yl)isonicotinic acid methyl ester obtained above was dissolved in pyridine (16 mL), hydroxyammonium chloride (134 mg, 1.93 mmol) was added, and the mixture was heated for 2 h while being stirred under reflux. After completion of the reaction, the solvent was concentrated under reduced pressure, ethyl acetate was added to the residue, which was then washed with aqueous sodium chloride solution. The organic layer was dried over anhydrous magnesium sulfate and concentrated under reduced pressure. The resulting solid was washed with ethyl acetate and dried to give 2-{3-[(E,Z)-hydroxyiminomethyl]-1H-indol-5-yl}isonicotinic acid methyl ester.

2-{3-[(E,Z)-hydroxyiminomethyl]-1H-indol-5-yl}isonicotinic acid methyl ester obtained above and di(imidazol-1-yl)methanthione (0.8 g, 4.48 mmol) were dissolved in tetrahydrofuran (30 mL) and stirred for 2 h at room temperature. After completion of the reaction, ethyl acetate was added to the reaction solution, which was then washed with aqueous sodium chloride solution. The organic layer was separated, dried over anhydrous magnesium sulfate, filtered and purified by column chromatography to give the title compound (0.36 g, 1.30 mmol, 76% Yield).

NMR: $^1$H-NMR (CDCl$_3$) δ 8.98 (1H, br), 8.90 (1H, d), 8.50 (1H, s), 8.42 (1H, s), 8.17 (1H, dd), 7.83 (2H, m), 7.62 (1H, d), 4.07 (3H, s)

Mass (EI) 278 (M$^+$+1)

Preparation 38: Synthesis of 2-(3-cyano-1-isopropyl-indol-5-yl)isonicotinic acid isopropyl ester

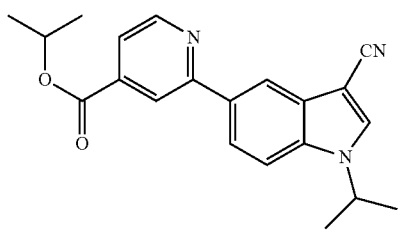 [SMILES: CC(C)OC(=O)c1ccnc(-c2ccc3c(c2)c(C#N)cn3C(C)C)c1]

2-(3-Cyano-1H-indol-5-yl)isonicotinic acid methyl ester (13 mg, 0.047 mmol) obtained in Preparation 37 was dissolved in N,N-dimethylformamide (0.5 mL). Sodium hydride (3 mg, 0.068 mmol) was added at 0° C., and stirred for 10 min at room temperature. 2-Iodopropane (0.02 mL, 0.23 mmol) was added, and stirred for 2 h at room temperature. After completion of the reaction, the solution was concentrated under reduced pressure, ethyl acetate (50 mL) was added, and washed with aqueous ammonium chloride solution. The organic layer was separated, dried over anhydrous magnesium sulfate, filtered and purified by column chromatography to give the title compound (13 mg, 0.037 mmol, 80% Yield).

NMR: $^1$H-NMR (CDCl$_3$) δ 8.84 (1H, d), 8.43 (1H, d), 8.34 (1H, m), 8.11 (1H, dd), 7.79 (1H, dd), 7.77 (1H, s), 7.56 (1H, d), 5.34 (1H, m), 4.75 (1H, m), 1.58 (6H, d), 1.44 (6H, d)

Mass (EI) 348 (M$^+$+1)

Preparation 39: Synthesis of 2-[3-cyano-1-[1-(methacryloxy)propan-2-yl]-indol-5-yl]isonicotinic acid methyl ester

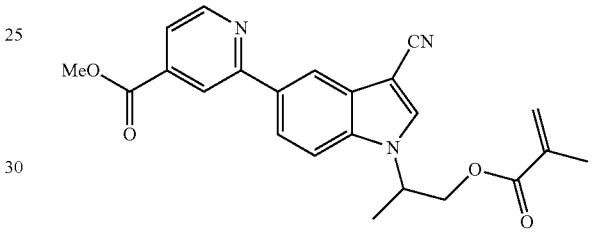

2-(3-Cyano-1H-indol-5-yl)isonicotinic acid methyl ester (250 mg, 0.90 mmol) obtained in Preparation 37, 2-methylsulfonyloxypropyl 2-methylprop-2-enoate (500 mg, 2.25 mmol) and sodium hydride (78 mg, 1.8 mmol) were reacted according to the same procedure as Preparation 5 to give the title compound (140 mg, 0.34 mmol, 40% Yield).

NMR: $^1$H-NMR (CDCl$_3$)(1:1 mixture) δ 8.86 (2H, m), 8.44 (2H, m), 8.38 (2H, m), 8.14 (2H, m), 7.78 (2H, m), 7.77 (1H, s), 7.64 (1H, s), 7.58 (1H, s), 7.56 (1H, s), 6.05 (1H, s), 5.93 (1H, s), 5.59 (1H, m), 5.52 (1H, m), 5.35 (1H, m), 4.97 (1H, m), 4.45 (1H, s), 4.43 (1H, s), 4.38 (1H, d), 4.35 (1H, d), 4.03 (6H, s), 1.88 (3H, m), 1.82 (3H, m), 1.70 (2H, d), 1.34 (2H, d)

Mass (EI) 404 (M$^+$+1)

Preparation 40: Synthesis of 2-[3-cyano-1-(hydroxypropan-2-yl-indol-5-yl)isonicotinic acid

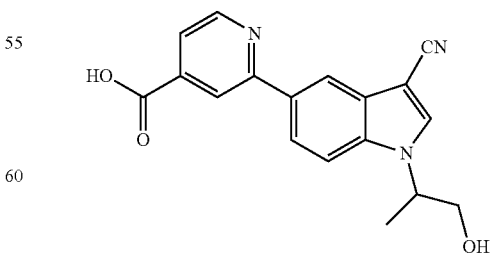

To 2-{3-cyano-1-[1-(methacryloxy)propan-2-yl]-indol-5-yl}isonicotinic acid methyl ester (140 mg, 0.34 mmol) obtained in Preparation 39 were added tetrahydrofuran (5.0 mL), water (5.0 mL) and methanol (5.0 mL), and dissolved. Sodium hydroxide (280 mg, 6.8 mmol) was added and stirred for 1 h at room temperature. 1N-aqueous hydrochloric acid solution was added to give a solid which was then filtered to give the title compound (96 mg, 0.29 mmol, 86% Yield).

Mass (EI) 322 (M$^+$+1)

Preparation 41: Synthesis of 2-[3-cyano-1-(1-fluoro-propan-2-yl)-indol-5-yl]isonicotinic acid ethyl ester

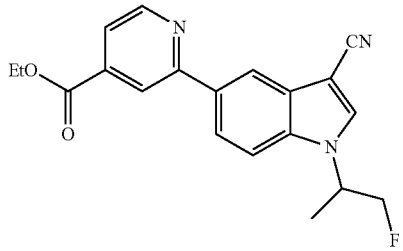

2-[3-Cyano-1-(hydroxypropan-2-yl-indol-5-yl)isonicotinic acid (96 mg, 0.29 mmol) obtained in Preparation 40 was dissolved in N,N-dimethylformamide (6 mL), and potassium carbonate (62 mg, 0.43 mmol) and bromoethane (0.07 mL, 0.86 mmol) were added thereto. The solution was stirred for 12 h at room temperature and concentrated under reduced pressure. Saturated ammonium chloride solution (5 mL) was added and ethyl acetate (20 mL) was added. The organic layer was separated, dried over anhydrous magnesium sulfate and filtered. The solvent was removed and the residue was purified by column chromatography to give 2-[3-cyano-1-(hydroxypropan-2-yl-indol-5-yl)isonicotinic acid ethyl ester (70 mg, 0.20 mmol, 67% Yield). Dichloromethane (4 mL) was added thereto, (dimethylamino)sulfur trifluoride (0.04 mL, 0.30 mmol) was added, and the mixture was stirred for 2 h at room temperature. After completion of the reaction, ethyl acetate was added. The mixture was washed with aqueous sodium chloride solution, dried over anhydrous magnesium sulfate and filtered. The solvent was removed and the residue was purified by column chromatography to give the title compound (39 mg, 0.11 mmol, 55% Yield).

NMR: $^1$H-NMR (CDCl$_3$) (1:1 mixture) δ 8.84 (2H, m), 8.43 (2H, m), 8.36 (2H, s), 8.14 (1H, m), 8.12 (1H, m), 7.79 (2H, m), 7.71 (1H, m), 7.49 (1H, m), 5.09~4.28 (6H, m), 4.47 (4H, q), 1.70 (3H, d), 1.46 (6H, t), 1.38 (3H, d)

Mass (EI) 352 (M$^+$+1)

Preparation 42: Synthesis of 2-[3-cyano-1-(2-methoxyethyl)-indol-5-yl]isonicotinic acid methyl ester

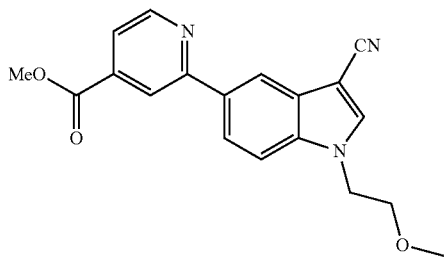 [SMILES: COCCn1cc(C#N)c2cc(-c3cc(C(=O)OC)ccn3)ccc21]

2-(3-Cyano-1H-indol-5-yl)isonicotinic acid methyl ester (65 mg, 0.023 mmol) obtained in Preparation 37 was reacted according to the same procedure as Preparation 5 to give the title compound (44 mg, 0.13 mmol, 57% Yield).

NMR: $^1$H-NMR (CDCl$_3$) δ 8.85 (1H, dd), 8.43 (1H, m), 8.37 (1H, m), 8.12 (1H, dd), 7.78 (1H, dd), 7.75 (1H, s), 7.52 (1H, d), 4.35 (2H, t), 4.02 (3H, s), 3.74 (2H, t), 3.35 (3H, s)

Mass (EI) 336 (M$^+$+1)

Preparation 43: Synthesis of 2-(1H-indol-5-yl)-6-methylisonicotinic acid methyl ester

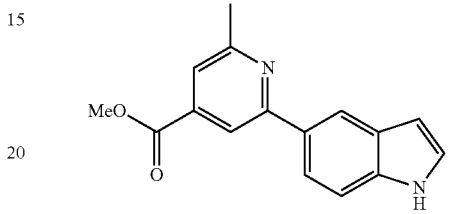

2-Chloro-6-methylisonicotinic acid methyl ester (1 g, 5.38 mmol) was reacted according to the same procedure as Preparation 36 to give the title compound (420 mg, 1.57 mmol, 29% Yield).

NMR: $^1$H-NMR (CDCl$_3$) δ 8.35 (1H, m), 8.22 (1H, br), 7.94 (1H, dd), 7.59 (1H, m), 7.48 (2H, m), 6.65 (1H, m), 3.98 (3H, s), 2.70 (3H, s)

Mass (EI) 267 (M$^+$+1)

Preparation 44: Synthesis of 2-(3-formyl-1H-indol-5-yl)-6-methylisonicotinic acid methyl ester

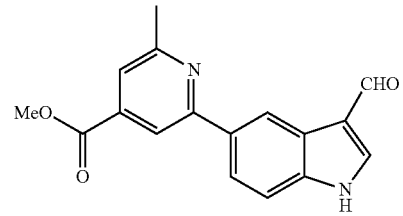 [SMILES: COC(=O)c1cc(C)nc(-c2ccc3[nH]cc(C=O)c3c2)c1]

2-(1H-indol-5-yl)-6-methylisonicotinic acid methyl ester (420 mg, 1.57 mmol) obtained in Preparation 43 was reacted according to the same procedure as Process (1) of Preparation 2 to give the title compound (350 mg, 1.18 mmol, 75% Yield).

NMR: $^1$H-NMR (CDCl$_3$) δ 10.12 (1H, s), 8.93 (1H, s), 8.89 (1H, br), 8.20 (1H, d), 8.13 (1H, dd), 7.89 (1H, d), 7.65 (1H, s), 7.53 (1H, d), 4.00 (3H, s), 2.71 (3H, s)

Mass (EI) 295 (M$^+$+1)

Preparation 45: Synthesis of 2-(3-cyano-1H-indol-5-yl)-6-methylisonicotinic acid methyl ester

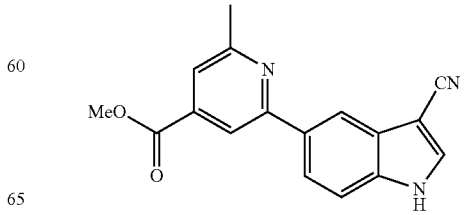

2-(3-Formyl-1H-indol-5-yl)-6-methylisonicotinic acid methyl ester (350 mg, 1.18 mmol) obtained in Preparation 44 was reacted according to the same procedure as Process (2) of Preparation 2 to give 2-{3-[(E,Z)-hydroxyiminomethyl]-1H-indol-5-yl}-6-methylisonicotinic acid methyl ester. This compound was reacted according to the same procedure as Process (3) of Preparation 2 to give the title compound (220 mg, 0.76 mmol, 64% Yield).

NMR: $^1$H-NMR (CD$_3$OD) δ 8.32 (1H, s), 8.18 (1H, s), 8.04 (1H, s), 7.95 (1H, d), 7.72 (1H, s), 7.65 (1H, d), 4.00 (3H, s), 2.71 (3H, s)

Mass (EI) 292 (M$^+$+1)

Preparation 46: Synthesis of 2-(3-cyano-1-isopropyl-indol-5-yl)-6-methylisonicotinic acid isopropyl ester

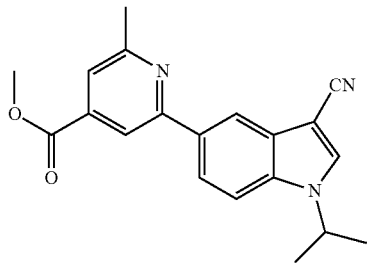 [SMILES: COC(=O)c1cc(C)nc(-c2ccc3c(c2)c(C#N)cn3C(C)C)c1]

2-(3-Cyano-indol-5-yl)-6-methylisonicotinic acid methyl ester (100 mg, 0.34 mmol) obtained in Preparation 45 was reacted according to the same procedure as Preparation 5 to give the title compound (80 mg, 0.22 mmol, 64% Yield).

NMR: $^1$H-NMR (CDCl$_3$) δ 8.44 (1H, d), 8.12 (1H, s), 8.08 (1H, dd), 7.75 (1H, s), 7.64 (1H, s), 7.53 (1H, d), 5.32 (1H, m), 4.60 (1H, m), 2.82 (3H, s), 1.60 (6H, d), 1.37 (6H, d)

Mass (EI) 362 (M$^+$+1)

Preparation 47: Synthesis of 2-(1H-indol-5-yl)isonicotinic acid ethyl ester

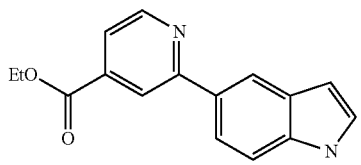 [SMILES: CCOC(=O)c1ccnc(-c2ccc3[nH]ccc3c2)c1]

2-Bromoisonicotinic acid ethyl ester (2 g, 8.66 mmol) was reacted according to the same procedure as Preparation 1 to give the title compound (1.4 g, 5.25 mmol, 60% Yield).

NMR: $^1$H-NMR (CDCl$_3$) δ 8.81 (1H, d), 8.35 (3H, br), 7.94 (1H, dd), 7.72 (1H, dd), 7.49 (1H, d), 7.25 (1H, m), 6.65 (1H, m), 4.45 (2H, q), 1.44 (3H, t)

Mass (EI) 267 (M$^+$+1)

Preparation 48: Synthesis of 2-[1-(phenylsulfonyl)-indol-5-yl]isonicotinic acid ethyl ester

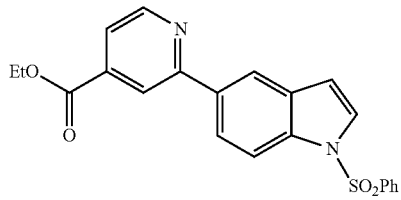

2-(1H-indol-5-yl)isonicotinic acid ethyl ester (1.4 g, 5.25 mmol) obtained in Preparation 47 was dissolved in N,N-dimethylformamide (25 mL) and cooled to 0° C. Sodium hydride (460 mg, 10.5 mmol) and phenylsulfonylchloride (0.8 mL, 6.3 mmol) were added and stirred for 12 h at room temperature. After completion of the reaction, the reaction solution was concentrated under reduced pressure, ethyl acetate (100 mL) was added, and washed with aqueous ammonium chloride solution. The organic layer was separated, dried over anhydrous magnesium sulfate, filtered, dried under reduced pressure and purified by column chromatography to give the title compound (1.2 g, 2.95 mmol, 56% Yield).

NMR: $^1$H-NMR (CDCl$_3$) δ 8.81 (1H, dd), 8.29 (1H, m), 8.22 (1H, m), 8.11 (1H, d), 8.02 (1H, dd), 7.89 (2H, m), 7.76 (1H, dd), 7.61 (1H, d), 7.54 (1H, m), 7.44 (2H, t), 6.76 (1H, d), 4.45 (2H, q), 1.44 (3H, t)

Mass (EI) 407 (M$^+$+1)

Preparation 49: Synthesis of 2-[3-nitro-1-(phenylsulfonyl)-indol-5-yl]isonicotinic acid ethyl ester

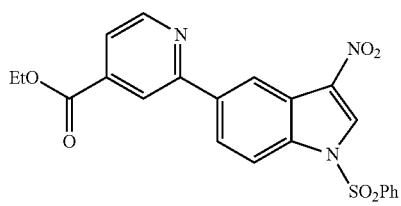

2-[1-(Phenylsulfonyl)-indol-5-yl]isonicotinic acid ethyl ester (300 mg, 0.73 mmol) obtained in Preparation 48 was dissolved in acetic anhydride (4 mL) and nitric acid (90%, red fuming, 0.1 mL, 2.2 mmol) was slowly added thereto. The mixture was stirred for 12 h at room temperature and poured to ice water (100 mL). Ethyl acetate (100 mL) was added to separate the organic layer which was then dried over anhydrous magnesium sulfate. The resulting solid was filtered to give the title compound (330 mg, 0.72 mmol, 99% Yield).

NMR: $^1$H-NMR (CDCl$_3$) δ 9.12 (1H, d), 8.76 (1H, d), 8.67 (1H, s), 8.57 (1H, d), 8.26 (1H, d), 8.22 (1H, dd), 8.11 (1H, m), 8.05 (2H, m), 7.71 (1H, t), 7.60 (2H, t), 4.55 (2H, t), 1.49 (3H, t)

Mass (EI) 452 (M$^+$+1)

Preparation 50: Synthesis of 2-(3-nitro-1H-indol-5-yl) isonicotinic acid

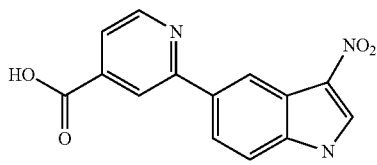 [SMILES: O=C(O)c1ccnc(-c2ccc3[nH]cc([N+](=O)[O-])c3c2)c1]

2-[3-Nitro-1-(phenylsulfonyl)-1H-indol-5-yl]isonicotinic acid ethyl ester (330 mg, 0.72 mmol) obtained in Preparation 49 was reacted according to the same procedure as Preparation 40 to give the title compound (200 mg, 0.7 mmol, 97% Yield).

Mass (EI) 284 (M$^+$+1)

Preparation 51: Synthesis of 2-(1-isopropyl-3-nitro-indol-5-yl) isonicotinic acid isopropyl ester

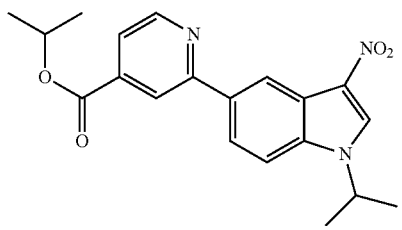 [SMILES: CC(C)OC(=O)c1ccnc(-c2ccc3c(c2)c([N+](=O)[O-])cn3C(C)C)c1]

2-(3-Nitro-1H-indol-5-yl)isonicotinic acid (200 mg, 0.7 mmol) obtained in Preparation 50 was dissolved in acetonitrile (5 mL). Cesium carbonate (450 mg, 1.4 mmol) and 2-iodopropane (0.7 mL, 7 mmol) were added, and stirred under reflux for 2 h at 80° C. After completion of the reaction, the reaction solution was concentrated under reduced pressure and purified by column chromatography to give the title compound (200 mg, 0.54 mmol, 80% Yield).

Mass (EI) 368 (M$^+$+1)

Preparation 52: Synthesis of 2-amino-5-iodo-benzonitrile

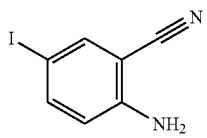

2-Amino-benzonitrile (10 g, 0.085 mol) and ammonium iodide (13.5 g, 0.094 mol) were dissolved in acetic acid (200 mL). 30% aqueous hydrogen peroxide solution (5.3 mL, 0.094 mL) was slowly added at room temperature and stirred for 12 h. After completion of the reaction, the reaction solution was filtered through celite. The filtrate was treated with aqueous sodium thiosulfate solution and extracted with ethyl acetate. The organic layer was dried over sodium sulfate and filtered. The solid obtained using dichloromethane (10 mL) and hexane (200 mL) was filtered and dried under nitrogen gas to give the title compound (10 g, Yield 48%).

NMR: $^1$H-NMR (CDCl$_3$) δ 7.64 (1H, d), 7.56 (1H, dd), 6.35 (1H, d), 4.44 (2H, br s)

Mass (EI) 245 (M$^+$+1)

Preparation 53: Synthesis of 1-(4-amino-3-cyano-phenyl)-pyrazole-4-carboxylic acid ethyl ester

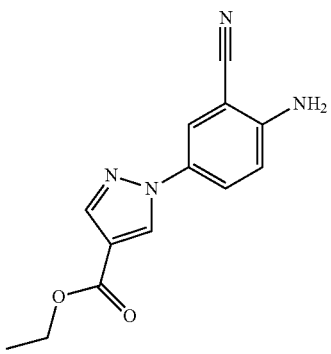 [SMILES: CCOC(=O)c1cnn(-c2ccc(N)c(C#N)c2)c1]

2-Amino-5-iodo-benzonitrile (5 g, 20 mmol) obtained in Preparation 52 was dissolved in toluene (40 mL). At room temperature, 1H-pyrazole-4-carboxylic acid ethyl ester (2.3 g, 16.7 mmol), copper iodide (0.323 g, 1.7 mmol), potassium carbonate (4.9 g, 36 mmol) and N,N-dimethyl-ethane-1,2-diamine (0.37 mL, 3.4 mmol) were added and refluxed for 24 h. The solution was filtered through celite using ethyl acetate, and the solvent was distilled off. The solid obtained using dichloromethane and methanol was filtered and dried under nitrogen gas to give the title compound (2.95 g, Yield 56%).

NMR: $^1$H-NMR (CDCl$_3$) δ 8.25 (1H, s), 8.05 (1H, s), 7.72 (1H, d), 7.71-7.57 (2H, m), 6.84 (1H, d), 4.55 (2H, br s), 4.35-4.30 (2H, q), 1.37 (3H, t)

Mass (EI) 257 (M$^+$+1)

Preparation 54: Synthesis of 1-(4-amino-3-cyano-5-iodo-phenyl)-pyrazole-4-carboxylic acid ethyl ester

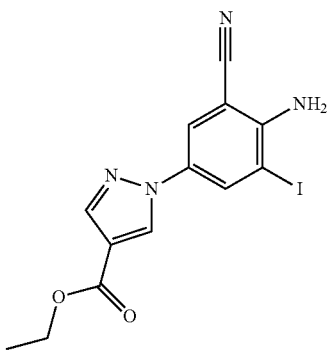 [SMILES: CCOC(=O)c1cnn(-c2cc(I)c(N)c(C#N)c2)c1]

1-(4-Amino-3-cyano-phenyl)-pyrazole-3-carboxylic acid ethyl ester (2.1 g, 8.2 mmol) obtained in Preparation 53, iodine (3.1 g, 12.3 mmol) and silver nitrate (2.55 g, 8.2 mmol) were added to ethanol (50 mL) and reacted for 12 h at room temperature. After reaction, the solution was filtered through celite using ethanol. After filtration, sodium thiosulfate (20 mL) was added, and ethyl acetate (100 mL) was added. The organic layer was separated and dried over anhydrous magnesium sulfate. All the solvent was removed. The solid was obtained using hexane and dichloromethane, filtered and dried under nitrogen gas to give the title compound (1.5 g, 49% Yield).

NMR: $^1$H-NMR (CDCl$_3$) δ 8.29 (1H, s), 8.26 (1H, d), 8.10 (1H, s), 7.78 (1H, d), 5.05 (2H, br s), 4.41-4.35 (2H, q), 1.42 (3H, t)

Mass (EI) 383 (M$^+$+1)

Preparation 55: Synthesis of 1-(4-amino-3-cyano-5-phenylethenyl)-pyrazole-4-carboxylic acid ethyl ester

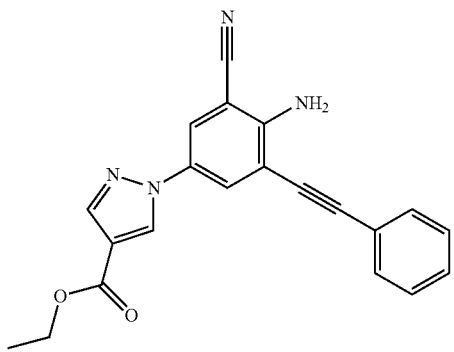 [SMILES: CCOC(=O)c1cnn(-c2cc(C#N)c(N)c(C#Cc3ccccc3)c2)c1]

1-(4-Amino-3-cyano-5-iodo-phenyl)-pyrazole-4-carboxylic acid ethyl ester (0.038 g, 0.1 mmol) obtained in Preparation 54, dichlorobis(triphenylphosphine) palladium (0.035 g, 0.05 mmol), copper iodide (2 mg, 0.01 mmol), ethinyl-benzene (0.055 mL, 0.5 mmol) and triethylamine (0.07 mL, 0.5 mmol) were added to tetrahydrofuran (5 mL), and reacted for 3 h at room temperature. After reaction, the solution was filtered through celite using ethyl acetate. After filtration, 1N aqueous hydrochloric acid solution (10 mL) was added, and ethyl acetate (10 mL) was added. The organic layer was separated, dried over anhydrous magnesium sulfate, filtered and purified by column chromatography to give the title compound (0.03 g, Yield 82%).

NMR: $^1$H-NMR (CDCl$_3$) δ 8.29 (1H, s), 8.26 (1H, d), 8.10 (1H, s), 7.78 (1H, d), 5.05 (2H, br s), 4.41-4.35 (2H, q), 1.42 (3H, t)

Mass (EI) 357 (M$^+$+1)

Preparation 56: Synthesis of 1-(7-cyano-2-phenyl-1H-indol-5-yl)-pyrazole-4-carboxylic acid ethyl ester

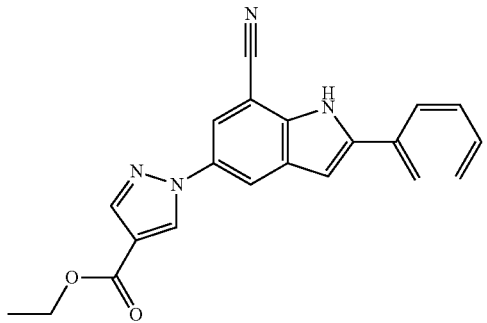 [SMILES: C=C/C=C\C(=C)c1cc2cc(-n3cc(C(=O)OCC)cn3)cc(C#N)c2[nH]1]

1-(4-Amino-3-cyano-5-phenylethenyl)-pyrazole-4-carboxylic acid ethyl ester (0.03 g, 0.084 mmol) obtained in Preparation 55 was dissolved in 1-methyl-2-pyrrolidinone (NMP) (3 mL). At room temperature, potassium t-butoxide (0.014 g, 0.13 mmol) was added and stirred for 1 h. After reaction, ethyl acetate (20 mL) was added and washed with water. The organic layer was separated, dried over magnesium sulfate, filtered and purified by column chromatography to give the title compound (0.02 g, 67% Yield).

NMR: $^1$H-NMR (CDCl$_3$) δ 9.60 (1H, d), 8.41 (1H, s), 8.11 (1H, s), 8.10 (1H, s), 7.85 (1H, s), 7.71-7.41 (5H, m), 6.94 (1H, d), 4.36-4.32 (2H, q), 1.38 (3H, t)

Mass (EI) 357 (M$^+$+1)

Preparation 57: Synthesis of 1-[4-amino-3-cyano-5-(3-methyl-1-butinyl)-phenyl]-pyrazole-4-carboxylic acid ethyl ester

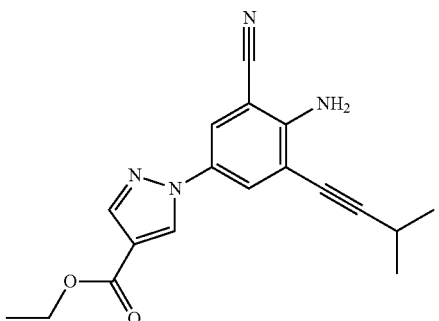

1-(4-Amino-3-cyano-5-iodo-phenyl)-pyrazole-4-carboxylic acid ethyl ester (0.1 g, 0.27 mmol) obtained in Preparation 54 and 3-methyl-1-butine (0.057 mL, 0.23 mmol) were reacted according to the same procedure as Preparation 55 to give the title compound (0.06 g, 69% Yield).

NMR: $^1$H-NMR (CDCl$_3$) δ 8.25 (1H, s), 8.05 (1H, s), 7.75 (1H, d), 7.66 (1H, d), 5.02 (2H, br s), 4.34-4.30 (2H, q), 2.87-2.84 (1H, m), 1.36 (3H, t), 1.31 (6H, d)

Mass (EI) 323 (M$^+$+1)

Preparation 58: Synthesis of 1-[4-amino-3-cyano-5-(3-methoxy-1-propinyl)-phenyl]-pyrazole-4-carboxylic acid ethyl ester

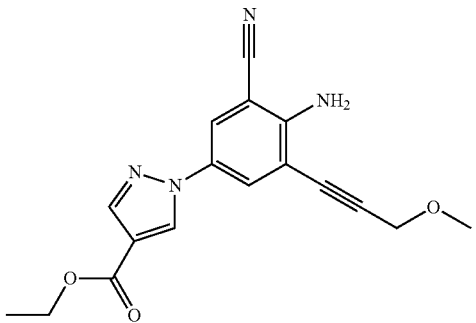 [SMILES: CCOC(=O)c1cnn(-c2cc(C#N)c(N)c(C#CCOC)c2)c1]

1-(4-Amino-3-cyano-5-iodo-phenyl)-pyrazole-4-carboxylic acid ethyl ester (0.2 g, 0.54 mmol) obtained in Preparation 54 and 3-methoxy-propione (0.068 mL, 0.81 mmol)

were reacted according to the same procedure as Preparation 55 to give the title compound (0.16 g, 91% Yield).

NMR: $^1$H-NMR (CDCl$_3$) δ 8.24 (1H, s), 8.02 (1H, s), 7.78 (1H, d), 7.69 (1H, d), 4.36 (2H, s), 4.32-4.28 (2H, q), 3.44 (3H, s), 3.37 (2H, s), 1.33 (3H, t)

Mass (EI) 325 (M$^+$+1)

Preparation 59: Synthesis of 1-(4-amino-3-cyano-5-trimethylsilanylethinyl-phenyl)-pyrazole-4-carboxylic acid ethyl ester

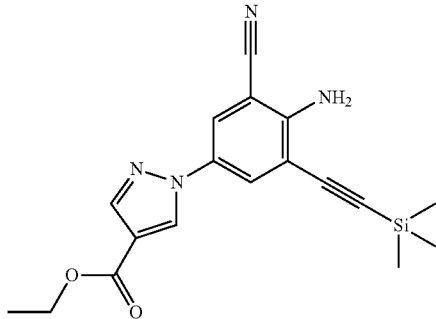 [SMILES: CCOC(=O)c1cnn(-c2cc(C#N)c(N)c(C#C[Si](C)(C)C)c2)c1]

1-(4-Amino-3-cyano-5-iodo-phenyl)-pyrazole-4-carboxylic acid ethyl ester (0.1 g, 0.27 mmol) obtained in Preparation 54 and ethinyl-trimethyl-silane (0.057 mL, 0.41 mmol) were reacted according to the same procedure as Preparation 55 to give the title compound (0.16 g, 91% Yield).

NMR: $^1$H-NMR (CDCl$_3$) δ 8.25 (1H, s), 8.05 (1H, s), 7.81 (1H, d), 7.71 (1H, d), 5.09 (2H, br s), 4.34-4.30 (2H, q), 1.36 (3H, t), 0.27 (9H, s)

Mass (EI) 353 (M$^+$+1)

Preparation 60: Synthesis of 1-(4-amino-3-cyano-5-ethinyl-phenyl)-pyrazole-4-carboxylic acid ethyl ester

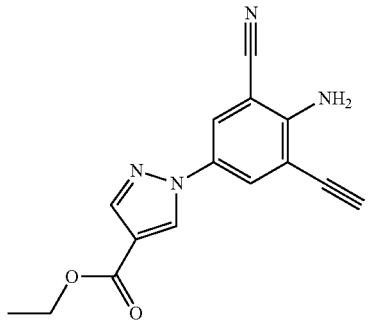 [SMILES: C#Cc1cc(-n2cc(C(=O)OCC)cn2)cc(C#N)c1N]

1-(4-Amino-3-cyano-5-trimethylsilanylethinyl-phenyl)-pyrazole-4-carboxylic acid ethyl ester (0.06 g, 0.18 mmol) obtained in Preparation 59 was dissolved in methanol (10 mL). Potassium carbonate (2.5 mg, 0.018 mmol) was added at room temperature and stirred for 3 h. The resulting solid was washed with water, filtered and dried under nitrogen gas to give the title compound (40 mg, 81% Yield).

NMR: $^1$H-NMR (CDCl$_3$) δ 8.25 (1H, s), 8.06 (1H, s), 7.84 (1H, d), 7.75 (1H, d), 5.12 (2H, br s), 4.34-4.30 (2H, q), 3.56 (1H, s), 1.37 (3H, t)

Mass (EI) 281 (M$^+$+1)

Example 1

Synthesis of 1-(3-cyano-1-isopropyl-indol-5-yl)pyrazole-4-carboxylic acid

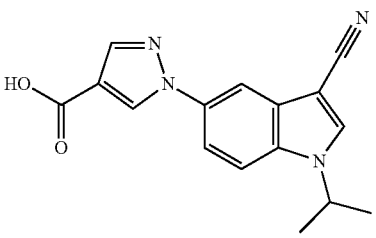 [SMILES: CC(C)n1cc(C#N)c2cc(-n3cc(C(=O)O)cn3)ccc21]

1-(3-Cyano-1-isopropyl-indol-5-yl)pyrazole-4-carboxylic acid ethyl ester (13.87 g, 43.03 mmol) obtained in Preparation 3 was added to tetrahydrofuran (140 mL), methanol (140 mL) and 6N sodium hydroxide solution (70 mL), which were then reacted for 1 h at room temperature. After reaction, the organic solvent was removed under reduced pressure, and the remaining aqueous layer was washed with ethyl acetate. Conc. hydrochloric acid was added to acidify the aqueous solution to pH 1. The precipitated solid was filtered, washed with distilled water and dried to give the title compound (12.09 g, 41.08 mmol, 95% Yield).

NMR: $^1$H-NMR (DMSO-d$_6$) δ 12.55 (1H, br), 9.10 (1H, s), 8.53 (1H, s), 8.16 (1H, d), 8.06 (1H, s), 7.90 (1H, dd), 7.86 (1H, d), 4.92-4.86 (1H, m), 1.48 (6H, d)

Mass (EI) 295 (M$^+$+1)

Example 2

Synthesis of 1-[3-cyano-1-(cyclopropylmethyl)indol-5-yl]pyrazole-4-carboxylic acid

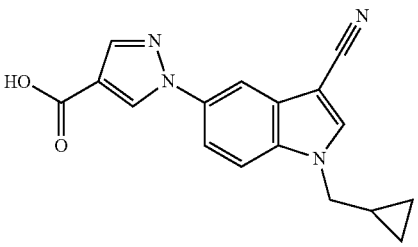 [SMILES: N#Cc1cn(CC2CC2)c2ccc(-n3cc(C(=O)O)cn3)cc12]

1-(3-Cyano-1H-indol-5-yl)pyrazole-4-carboxylic acid ethyl ester (94.3 mg, 0.36 mmol) obtained in Preparation 2 was dissolved in N,N-dimethylformamide (3.3 mL). Sodium hydride (55%, 22 mg, 0.50 mmol) was added at 0° C. and stirred for 10 min at room temperature. Bromomethylcyclopropane (0.04 mL, 0.41 mmol) was added and stirred for 15 h at room temperature. 6N sodium hydroxide solution (2 mL) was added to the solution, which was then reacted for 1 h at room temperature. The solvent was distilled under reduced pressure, and the residue was purified by column chromatography to give the title compound (23.1 mg, 0.075 mmol, 22% Yield).

NMR: $^1$H-NMR (DMSO-d$_6$) δ 9.05 (1H, s), 8.40 (1H, s), 8.11 (1H, d), 8.01 (1H, s), 7.85 (1H, dd), 7.82 (1H, d), 4.10 (2H, d), 1.26-1.22 (1H, m), 0.50-0.46 (2H, m), 0.39-0.35 (2H, m)

Mass (EI) 307 (M$^+$+1)

Example 3

Synthesis of 1-[3-cyano-1-cyclopropyl-indol-5-yl]pyrazole-4-carboxylic acid

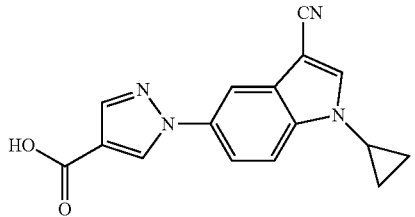 [SMILES: N#Cc1cn(C2CC2)c2ccc(-n3cc(C(=O)O)cn3)cc12]

1-(3-Cyano-1-cyclopropyl-indol-5-yl)pyrazole-4-carboxylic acid ethyl ester (120 mg, 0.37 mmol) obtained in Preparation 4 was reacted according to the same procedure as Example 1 to give the title compound (95 mg, 88% Yield).

NMR: $^1$H-NMR (DMSO-d$_6$) δ 12.56 (1H, b), 9.13 (1H, s), 8.40 (1H, s), 8.18 (1H, d), 8.08 (1H, s), 7.97 (1H, dd), 7.74 (1H d), 3.68-3.63 (1H, m), 1.15-1.11 (2H, m), 1.10-1.08 (2H, m)

Mass (EI) 293 (M$^+$+1)

Example 4

Synthesis of 1-(3-cyano-1-isobutyl-indol-5-yl)pyrazole-4-carboxylic acid

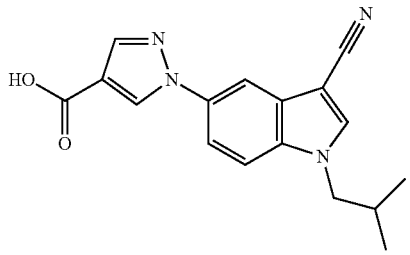 [SMILES: CC(C)Cn1cc(C#N)c2cc(-n3cc(C(=O)O)cn3)ccc21]

1-(3-Cyano-1H-indol-5-yl)pyrazole-4-carboxylic acid ethyl ester (92.3 mg, 0.33 mmol) obtained in Preparation 2, sodium hydride (55%, 22.0 mg, 0.50 mmol) and 1-bromo-2-methylpropane (0.04 mL, 0.37 mmol) were reacted according to the same procedure as Example 2 to give the title compound (25.5 mg, 0.083 mmol, 25% Yield).

NMR: $^1$H-NMR (DMSO-d$_6$) δ 9.08 (1H, s), 8.37 (1H, s), 8.15 (1H, d), 8.05 (1H, s), 7.88 (1H, dd), 7.85 (1H, d), 4.10 (2H, s), 2.18-2.12 (1H, m), 0.83 (6H, d)

Mass (EI) 309 (M$^+$+1)

Example 5

Synthesis of 1-[3-cyano-1-(2,2-dimethylpropyl)indol-5-yl]pyrazole-4-carboxylic acid

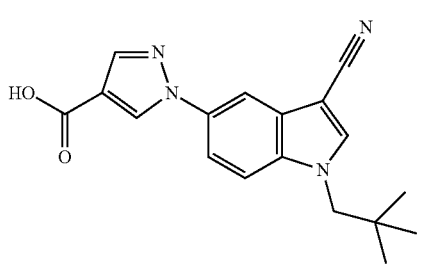 [SMILES: CC(C)(C)Cn1cc(C#N)c2cc(-n3cc(C(=O)O)cn3)ccc21]

1-(3-Cyano-1H-indol-5-yl)pyrazole-4-carboxylic acid ethyl ester (79.5 mg, 0.28 mmol) obtained in Preparation 2, sodium hydride (55%, 20.0 mg, 0.46 mmol) and 1-bromo-2,2-dimethylpropane (0.04 mL, 0.32 mmol) were reacted according to the same procedure as Example 2 to give the title compound (25.5 mg, 0.079 mmol, 28% Yield).

NMR: $^1$H-NMR (DMSO-d$_6$) δ 9.09 (1H, s), 8.31 (1H, s), 8.14 (1H, s), 8.05 (1H, s), 7.91-7.86 (2H, m), 4.11 (2H, s), 0.92 (9H, s)

Mass (EI) 323 (M$^+$+1)

Example 6

Synthesis of 1-[3-cyano-1-(2-methoxyethyl)indol-5-yl]pyrazole-4-carboxylic acid

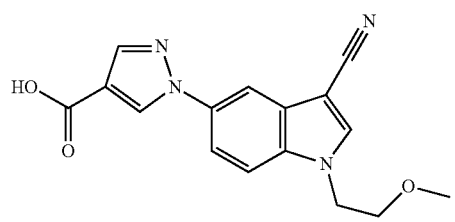 [SMILES: COCCn1cc(C#N)c2cc(-n3cc(C(=O)O)cn3)ccc21]

1-(3-Cyano-1H-indol-5-yl)pyrazole-4-carboxylic acid ethyl ester (96.7 mg, 0.34 mmol) obtained in Preparation 2, sodium hydride (55%, 22.6 mg, 0.52 mmol) and 2-bromoethylmethylether (0.05 mL, 0.53 mmol) were reacted according to the same procedure as Example 2 to give the title compound (48.0 mg, 0.155 mmol, 45% Yield).

NMR: $^1$H-NMR (DMSO-d$_6$) δ 9.09 (1H, s), 8.37 (1H, s), 8.18 (1H, d), 8.08 (1H, s), 7.93 (1H, dd), 7.87 (1H, d), 4.49 (2H, t), 3.72 (2H, t), 3.24 (3H, s)

Mass (EI) 311 (M$^+$+1)

Example 7

Synthesis of 1-(3-cyano-1-sec-butyl-indol-5-yl)-pyrazole-4-carboxylic acid

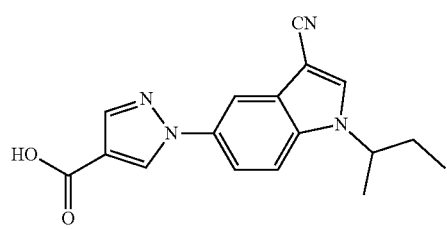 [SMILES: CCC(C)n1cc(C#N)c2cc(-n3cc(C(=O)O)cn3)ccc21]

1-(3-Cyano-1-sec-butyl-indol-5-yl)-pyrazole-4-carboxylic acid ethyl ester (102 mg, 0.3 mmol) obtained in Preparation 5 was reacted according to the same procedure as Example 1 to give the title compound (75 mg, 80% Yield).

NMR: $^1$H-NMR (CD$_3$OD) δ 8.76 (1H, s), 8.25 (1H, s), 8.11 (1H, s), 8.08 (1H, s), 7.80 (2H, s), 4.66 (1H, m), 2.01 (2H, m), 1.61 (3H, d), 0.91 (3H, t)

Mass (EI): 309 (M+1)

Example 8

Synthesis of 1-[3-cyano-1-cyclobutyl-indol-5-yl]pyrazole-4-carboxylic acid

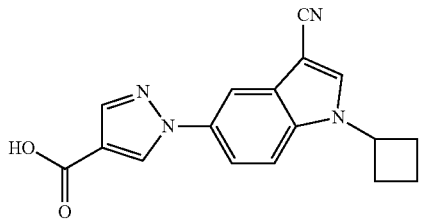 [SMILES: N#Cc1cn(C2CCC2)c2ccc(-n3cc(C(=O)O)cn3)cc12]

1-(3-Cyano-1-cyclobutyl-indol-5-yl)pyrazole-4-carboxylic acid ethyl ester (23 mg, 0.07 mmol) obtained in Preparation 6 was reacted according to the same procedure as Example 1 to give the title compound (10 mg, 48% Yield).

NMR: $^1$H-NMR (MeOD-d4) δ 8.76 (1H, d), 8.21 (1H, s), 8.12-8.07 (2H, m), 7.81-7.72 (2H, m), 4.18 (1H, d), 2.67-2.52 (1H, m), 1.42-1.26 (3H, m), 0.71-0.67 (1H, m), 0.52-0.48 (1H, m)

Mass (EI) 307 (M$^+$+1)

Example 9

Synthesis of 1-(3-cyano-1-cyclopentyl-indol-5-yl)-pyrazole-4-carboxylic acid

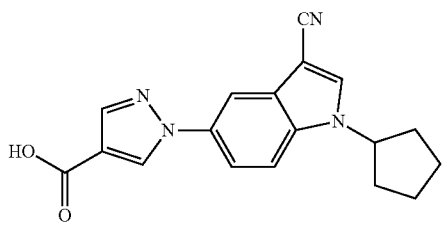 [SMILES: N#Cc1cn(C2CCCC2)c2ccc(-n3cc(C(=O)O)cn3)cc12]

1-(3-Cyano-1-cyclopentyl-indol-5-yl)-pyrazole-4-carboxylic acid ethyl ester (91 mg, 0.3 mmol) obtained in Preparation 7 was reacted according to the same procedure as Example 1 to give the title compound (68 mg, 81% Yield).

NMR: $^1$H-NMR (CD$_3$OD) δ 8.76 (1H, s), 8.23 (1H, s), 8.11 (1H, s), 8.06 (1H, s), 7.79 (2H, s), 4.99 (1H, m), 2.34 (2H, m), 2.00 (4H, m), 1.86 (2H, m)

Mass (EI): 321 (M+1)

Example 10

Synthesis of 1-[3-cyano-1-(1-fluoropropan-2-yl)-indol-5-yl]-pyrazole-4-carboxylic acid

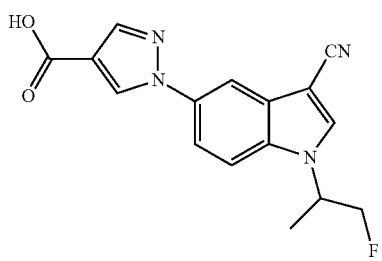 [SMILES: CC(CF)n1cc(C#N)c2cc(-n3cc(C(=O)O)cn3)ccc21]

1-[3-Cyano-1-(1-fluoropropan-2-yl)-indol-5-yl]-pyrazole-4-carboxylic acid ethyl ester (56 mg, 0.16 mmol) obtained in Preparation 10 was reacted according to the same procedure as Example 1 to give the title compound (48 mg, 0.15 mmol, 93% Yield).

NMR: $^1$H-NMR (DMSO-d$^6$) (1:1 mixture) δ 9.11 (2H, s), 8.58 (1H, s), 8.36 (1H, s), 8.19 (1H, s), 8.18 (1H, s), 8.07 (2H, s), 7.91 (4H, m), 5.20~4.50 (6H, m), 1.55 (3H, d), 1.35 (3H, m)

Mass (EI) 313 (M$^+$+1)

Example 11

Synthesis of 1-[3-cyano-1-(tetrahydrofuran-3-yl)-indol-5-yl]-pyrazole-4-carboxylic acid

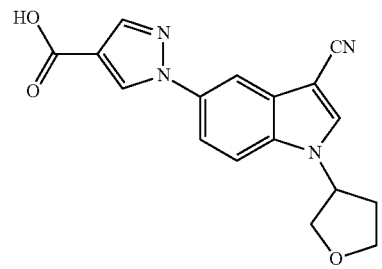 [SMILES: N#Cc1cn(C2CCOC2)c2ccc(-n3cc(C(=O)O)cn3)cc12]

1-[3-Cyano-1-(tetrahydrofuran-3-yl)-indol-5-yl]-pyrazole-4-carboxylic acid ethyl ester (150 mg, 0.53 mmol) obtained in Preparation 11 was reacted according to the same procedure as Example 1 to give the title compound (100 mg, 0.31 mmol, 72% Yield).

NMR: $^1$H-NMR (DMSO-d$^6$) δ 9.15 (1H, s), 8.42 (1H, s), 8.20 (1H, s), 8.09 (1H, s), 7.94 (2H, m), 5.40 (1H, m), 4.11 (1H, q), 3.97 (2H, d), 3.85 (1H, q), 2.60 (1H, m), 2.09 (1H, m)

Mass (EI) 323 (M$^+$+1)

Example 12

Synthesis of 1-[3-cyano-1-isopropyl-indol-5-yl]-3-methyl-pyrazole-4-carboxylic acid

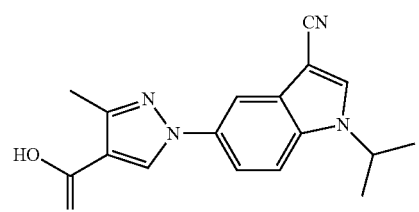

1-(3-Cyano-1-isopropyl-indol-5-yl)-3-methyl-pyrazole-4-carboxylic acid ethyl ester (150 mg, 0.45 mmol) obtained in Preparation 14 was reacted according to the same procedure as Example 1 to give the title compound (122 mg, 88% Yield).

NMR: $^1$H-NMR (DMSO-d$_6$) δ 9.04 (1H, s), 8.53 (1H, s), 8.13 (1H, s), 7.87 (2H, dd), 4.92-4.89 (1H, m), 2.46 (3H, s), 1.50 (6H, d)

Mass (EI) 309 (M$^+$+1)

Example 13

Synthesis of 1-[3-cyano-1-(cyclopropylmethyl)indol-5-yl]-3-methyl-pyrazole-4-carboxylic acid

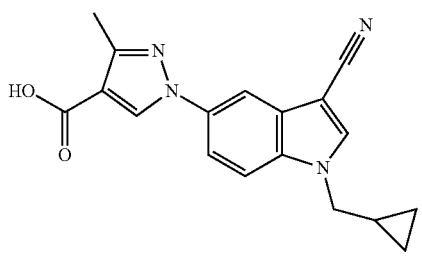 [SMILES: Cc1nn(-c2ccc3c(c2)c(C#N)cn3CC2CC2)cc1C(=O)O]

1-(3-Cyano-1H-indol-5-yl)-3-methyl-pyrazole-4-carboxylic acid ethyl ester (85.6 mg, 0.29 mmol) obtained in Preparation 13, sodium hydride (55%, 20 mg, 0.46 mmol) and bromomethylcyclopropane (0.04 mL, 0.41 mmol) were reacted according to the same procedure as Example 2 to give the title compound (30.4 mg, 0.095 mmol, 33% Yield).

NMR: $^1$H-NMR (DMSO-$d_6$) δ 9.01 (1H, s), 8.47 (1H, s), 8.15 (1H, d), 7.91 (1H, dd), 7.88 (1H, d), 4.18 (2H, d), 2.47 (3H, s), 1.36-1.30 (1H, m), 0.59-0.55 (2H, m), 0.48-0.44 (2H, m)

Mass (EI) 321 (M$^+$+1)

Example 14

Synthesis of 1-[3-cyano-1-(2-methoxyethyl)indol-5-yl]-3-methyl-pyrazole-4-carboxylic acid

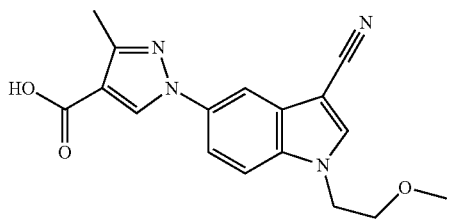 [SMILES: COCCn1cc(C#N)c2cc(-n3cc(C(=O)O)c(C)n3)ccc21]

1-(3-Cyano-1H-indol-5-yl)-3-methyl-pyrazole-4-carboxylic acid ethyl ester (88.8 mg, 0.30 mmol) obtained in Preparation 13, sodium hydride (55%, 20 mg, 0.46 mmol) and 2-bromoethylmethylether (0.04 mL, 0.43 mmol) were reacted according to the same procedure as Example 2 to give the title compound (63.9 mg, 0.197 mmol, 65% Yield).

NMR: $^1$H-NMR (DMSO-$d_6$) δ 9.01 (1H, s), 8.35 (1H, s), 8.14 (1H, d), 7.90 (1H, dd), 7.84 (1H, d), 4.48 (2H, t), 3.71 (2H, t), 3.24 (3H, s), 2.47 (3H, s)

Mass (EI) 325 (M$^+$+1)

Example 15

Synthesis of 1-[3-cyano-1-isopropyl-indol-5-yl]-3-(trifluoromethyl)pyrazole-4-carboxylic acid

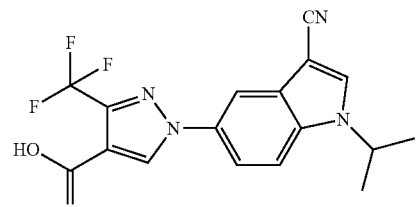

1-(3-Cyano-1-isopropyl-indol-5-yl)-3-(trifluoromethyl)pyrazole-4-carboxylic acid ethyl ester (130 mg, 0.33 mmol) obtained in Preparation 19 was reacted according to the same procedure as Example 1 to give the title compound (100 mg, 84% Yield).

NMR: $^1$H-NMR (DMSO-$d_6$) δ 9.34 (1H, s), 8.60 (1H, s), 8.24 (1H, s), 7.94 (2H, dd), 4.95-4.92 (1H, m), 1.51 (6H, d)

Mass (EI) 363 (M$^+$+1)

Example 16

Synthesis of 1-[3-cyano-1-(cyclopropylmethyl)indol-5-yl]-3-(trifluoromethyl)pyrazole-4-carboxylic acid

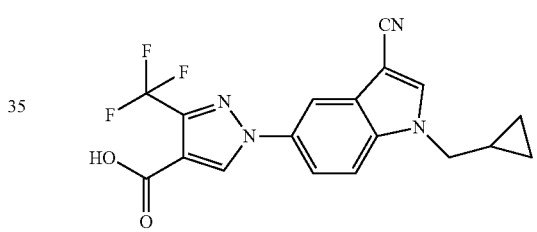

1-[3-Cyano-1-(cyclopropylmethyl)indol-5-yl]-3-(trifluoromethyl)pyrazole-4-carboxylic acid ethyl ester (130 mg, 0.33 mmol) obtained in Preparation 20 was reacted according to the same procedure as Example 1 to give the title compound (91 mg, 90% Yield).

NMR: $^1$H-NMR (DMSO-$d_6$) δ 9.34 (1H, s), 8.51 (1H, s), 8.24 (1H, s), 7.92 (2H, dd), 4.19 (2H, d), 1.32-1.23 (1H, m), 0.56 (2H, d), 0.45 (2H, d)

Mass (EI) 375 (M$^+$+1)

Example 17

Synthesis of 1-(1-isopropyl-3-nitro-indol-5-yl)pyrazole-4-carboxylic acid

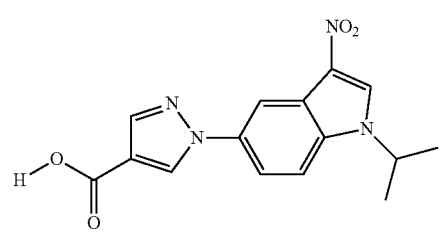 [SMILES: CC(C)n1cc([N+](=O)[O-])c2cc(-n3cc(C(=O)O)cn3)ccc21]

1-(1-Isopropyl-3-nitro-indol-5-yl)pyrazole-4-carboxylic acid ethyl ester (60.8 mg, 0.178 mmol) obtained in Preparation 22, tetrahydrofuran (2 mL), methanol (2 mL) and 6N sodium hydroxide solution (1 mL) were reacted according to the same procedure as Example 1 to give the title compound (35.8 mg, 0.114 mmol, 56% Yield).

NMR: $^1$H-NMR (DMSO-$d_6$) δ 9.05 (1H, s), 8.89 (1H, s), 8.55 (1H, m), 8.08 (1H, s), 7.95 (1H, d), 7.95 (1H, s), 4.99-4.92 (1H, m), 1.53 (6H, d)

Mass (EI) 315 (M$^+$+1)

Example 18

Synthesis of 1-(3-cyano-1-isopropyl-indol-5-yl)-1,2,4-triazole-3-carboxylic acid

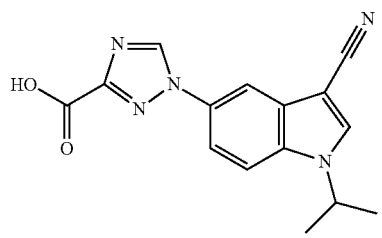 [SMILES: CC(C)n1cc(C#N)c2cc(-n3cnc(C(=O)O)n3)ccc21]

1-(3-Cyano-1-isopropyl-indol-5-yl)-1,2,4-triazole-3-carboxylic acid methyl ester obtained in Preparation 25, tetrahydrofuran (2 mL), methanol (2 mL) and 6N sodium hydroxide solution (1 mL) were reacted according to the same procedure as Example 1 to give the title compound (40.0 mg, 0.135 mmol, 46% Yield).

NMR: $^1$H-NMR (DMSO-$d_6$) δ 9.44 (1H, s), 8.59 (1H, s), 8.16 (1H, d), 7.95 (1H, d), 7.84 (1H, dd), 4.93-4.90 (1H, m), 1.49 (6H, d)

Mass (EI) 296 (M$^+$+1)

Example 19

Synthesis of 1-(3-cyano-1-isopropyl-indol-5-yl)imidazole-4-carboxylic acid

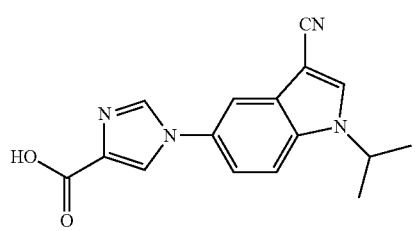 [SMILES: CC(C)n1cc(C#N)c2cc(-n3cnc(C(=O)O)c3)ccc21]

1-(3-Cyano-1-isopropyl-indol-5-yl)imidazole-4-carboxylic acid ethyl ester (86 mg, 0.26 mmol) obtained in Preparation 30 was reacted according to the same procedure as Example 1 to give the title compound (45 mg, 57% Yield).

NMR: $^1$H-NMR (CD$_3$OD) δ 9.06 (1H, s), 8.53 (1H, s), 8.35 (1H, s), 8.05 (1H, d), 7.92 (1H, d), 7.67 (1H, d), 4.96 (1H, m), 1.63 (6H, d)

Mass (EI): 295 (M+1)

Example 20

Synthesis of 5-(3-cyano-1-isopropyl-indol-5-yl)-thiophene-2-carboxylic acid

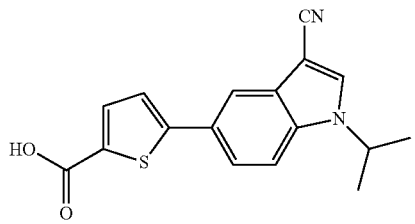 [SMILES: CC(C)n1cc(C#N)c2cc(-c3ccc(C(=O)O)s3)ccc21]

5-(3-Cyano-1-isopropyl-indol-5-yl)-thiophene-2-carboxylic acid methyl ester (183 mg, 0.56 mmol) obtained in Preparation 35 was reacted according to the same procedure as Example 1 to give the title compound (130 mg, 74% Yield).

NMR: $^1$H-NMR (CD$_3$OD) δ 8.20 (1H, s), 7.96 (1H, s), 7.78 (1H, d), 7.71 (2H, s), 7.48 (1H, d), 4.91 (1H, m), 1.61 (6H, d)

Mass (EI): 311 (M+1)

Example 21

Synthesis of 2-(3-cyano-1-isopropyl-indol-5-yl)isonicotinic acid

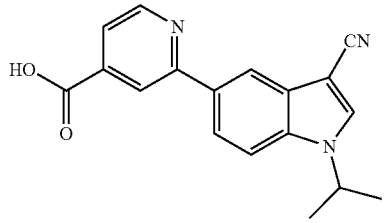 [SMILES: CC(C)n1cc(C#N)c2cc(-c3cc(C(=O)O)ccn3)ccc21]

2-(3-Cyano-1-isopropyl-indol-5-yl)isonicotinic acid isopropyl ester (13 mg, 0.037 mmol) obtained in Preparation 38 was added to tetrahydrofuran (1.0 mL), methanol (1.0 mL) and 1N-aqueous sodium hydroxide solution (1 mL), which were then reacted for 1 h at room temperature. After reaction, saturated aqueous ammonium chloride solution (3 mL) was added, and ethyl acetate (10 mL) was added. The organic layer was separated, dried over anhydrous magnesium sulfate, and filtered. The solvent was removed and the residue was purified by column chromatography to give the title compound (6 mg, 0.02 mmol, 54% Yield).

NMR: $^1$H-NMR (CD$_3$OD) δ 8.78 (1H, d), 8.42 (1H, s), 8.35 (1H, s), 8.23 (1H, s), 8.04 (1H, d), 7.85 (1H, d), 7.79 (1H, d), 4.95 (1H, m), 1.62 (6H, d)

Mass (EI) 306 (M$^+$+1)

Example 22

Synthesis of 2-[3-cyano-1-(cyclopropylmethyl)-indol-5-yl]isonicotinic acid

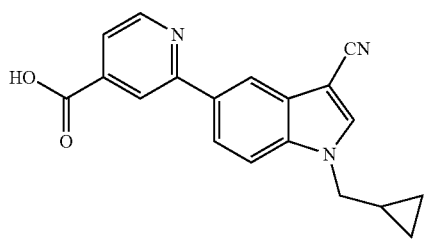 [SMILES: N#Cc1cn(CC2CC2)c2ccc(-c3cc(C(=O)O)ccn3)cc12]

2-(3-Cyano-indol-5-yl)isonicotinic acid methyl ester (100 mg, 0.36 mmol) obtained in Preparation 37 was dissolved in N,N-dimethylformamide (3.5 mL). Sodium hydride (23 mg, 0.54 mmol) was added at 0° C. and stirred for 10 min at room temperature. Bromomethyl(cyclopropane) (0.05 mL, 0.54 mmol) was added and stirred for 2 h at room temperature. The reaction solution was concentrated under reduced pressure, to which distilled water was added. The organic layer was separated, dried over anhydrous magnesium sulfate and filtered to give the title compound (25 mg, 0.078 mmol, 22% Yield).

NMR: $^1$H-NMR (DMSO-d$^6$) δ 8.87 (1H, d), 8.46 (1H, s), 8.43 (1H, d), 8.40 (1H, s), 8.14 (1H, dd), 7.88 (1H, d), 7.77 (1H, dd), 4.20 (2H, d), 1.25 (1H, m), 0.57 (2H, m), 0.47 (2H, m)

Mass (EI) 318 (M$^+$+1)

Example 23

Synthesis of 2-[3-cyano-1-(tetrahydrofuran-3-yl)-indol-5-yl]isonicotinic acid

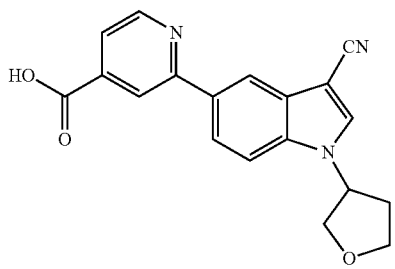 [SMILES: N#Cc1cn(C2CCOC2)c2ccc(-c3cc(C(=O)O)ccn3)cc12]

2-(3-Cyano-indol-5-yl)isonicotinic acid methyl ester (150 mg, 0.54 mmol) obtained in Preparation 37 was dissolved in N,N-dimethylformamide (5.4 mL). Sodium hydride (35 mg, 0.81 mmol) was added at 0° C. and stirred for 10 min at room temperature. Tetrahydrofuran-3-yl-methanesulfonate (180 mg, 1.08 mmol) was added and stirred under reflux for 16 h at 50° C. After completion of the reaction, the solution was concentrated under reduced pressure, ethyl acetate (50 mL) was added, and the mixture was washed with aqueous ammonium chloride solution. The organic layer was separated, dried over anhydrous magnesium sulfate and filtered to give 2-[3-cyano-1-(tetrahydrofuran-3-yl)-indol-5-yl]isonicotinic acid methyl ester. To this compound were added tetrahydrofuran (8 mL), methanol (8 mL) and 1N-aqueous sodium hydroxide solution (8 mL), and the mixture was stirred for 1 h at room temperature. After completion of the reaction, saturated aqueous ammonium chloride solution (5 mL) was added, and ethyl acetate (20 mL) was added. The organic layer was separated, dried over anhydrous magnesium sulfate and filtered. The solvent was removed and the residue was purified by column chromatography to give the title compound (53 mg, 0.16 mmol, 30% Yield).

NMR: $^1$H-NMR (DMSO-d$^6$) δ 8.87 (1H, d), 8.42 (1H, s), 8.33 (2H, s), 8.16 (1H, d), 7.91 (1H, d), 7.77 (1H, d), 5.41 (1H, m), 4.12 (4H, m), 4.00 (2H, d)

Mass (EI) 334 (M$^+$+1)

Example 24

Synthesis of 2-[3-cyano-1-(1-fluoropropan-2-yl)-indol-5-yl]isonicotinic acid

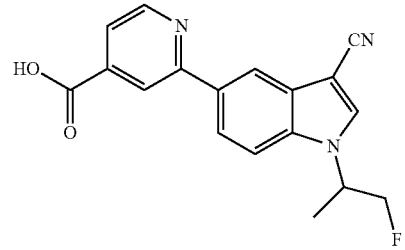 [SMILES: CC(CF)n1cc(C#N)c2cc(-c3cc(C(=O)O)ccn3)ccc21]

2-[3-Cyano-1-(1-fluoropropan-2-yl)-indol-5-yl]isonicotinic acid ethyl ester (39 mg, 0.11 mmol) obtained in Preparation 41 was reacted according to the same procedure as Example 1 to give the title compound (23 mg, 0.07 μmol, 65% Yield).

NMR: $^1$H-NMR (DMSO-d$^6$) (1:1 mixture) δ 8.87 (2H, m), 8.42 (6H, m), 8.14 (2H, m), 7.87 (2H, m), 7.78 (2H, m), 5.20~4.48 (6H, m), 1.3 (6H, m)

Mass (EI) 324 (M$^+$+1)

Example 25

Synthesis of 2-[3-cyano-1-(2-methoxyethyl)-indol-5-yl]isonicotinic acid

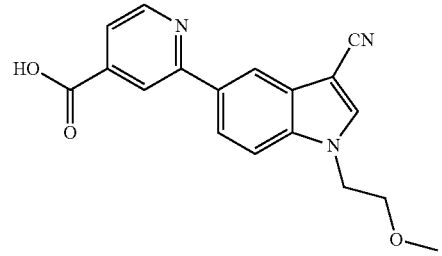 [SMILES: COCCn1cc(C#N)c2cc(-c3cc(C(=O)O)ccn3)ccc21]

2-[3-Cyano-1-(2-methoxyethyl)-indol-5-yl]isonicotinic acid methyl ester (44 mg, 0.13 mmol) obtained in Preparation 42 was reacted according to the same procedure as Example 1 to give the title compound (40 mg, 0.12 mmol, 92% Yield).

NMR: $^1$H-NMR (DMSO-d$^6$) δ 8.87 (1H, d), 8.40 (2H, m), 8.33 (1H, s), 8.13 (1H, dd), 7.84 (1H, d), 7.77 (1H, d), 4.49 (2H, t), 3.71 (2H, t), 3.23 (3H, s)

Mass (EI) 322 (M$^+$+1)

Example 26

Synthesis of 2-(3-cyano-1-isopropyl-indol-5-yl)-6-methylisonicotinic acid

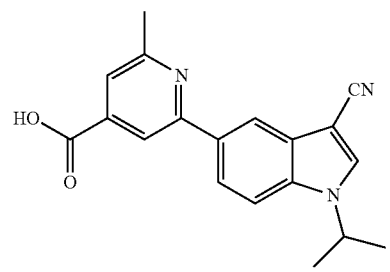 [SMILES: Cc1cc(C(=O)O)cc(-c2ccc3c(c2)c(C#N)cn3C(C)C)n1]

2-(3-Cyano-1-isopropyl-indol-5-yl)-6-methylisonicotinic acid isopropyl ester (80 mg, 0.22 mmol) obtained in Preparation 46 was reacted according to the same procedure as Example 1 to give the title compound (52 mg, 0.16 mmol, 72% Yield).

NMR: $^1$H-NMR (DMSO-d$^6$) δ 8.54 (1H, s), 8.39 (1H, d), 8.20 (1H, s), 8.09 (1H, dd), 7.87 (1H, d), 7.70 (1H, s), 4.92 (1H, m), 2.68 (3H, s), 1.52 (6H, d)

Mass (EI) 320 (M$^+$+1)

Example 27

Synthesis of 2-(1-isopropyl-3-nitro-indol-5-yl) isonicotinic acid

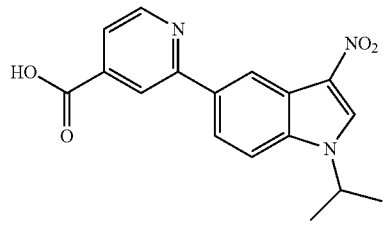 [SMILES: CC(C)n1cc([N+](=O)[O-])c2cc(-c3cc(C(=O)O)ccn3)ccc21]

2-(1-Isopropyl-3-nitro-indol-5-yl)isonicotinic acid isopropyl ester (200 mg, 0.54 mmol) obtained in Preparation 51 was reacted according to the same procedure as Example 1 to give the title compound (75 mg, 0.23 mmol, 42% Yield).

NMR: $^1$H-NMR (DMSO-d$^6$) δ 8.91 (2H, m), 8.88 (1H, d), 8.36 (1H, s), 8.18 (1H, dd), 7.95 (1H, d), 7.79 (1H, dd), 4.99 (1H, m), 1.57 (6H, d)

Mass (EI) 326 (M$^+$+1)

Example 28

Synthesis of 1-(7-cyano-2-phenyl-1H-indol-5-yl)-pyrazole-4-carboxylic acid

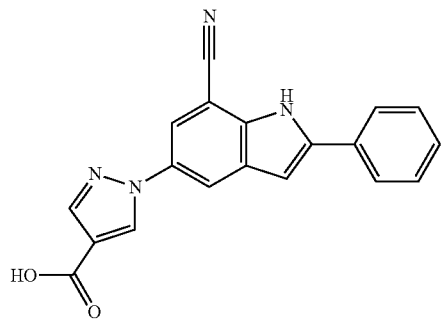 [SMILES: N#Cc1cc(-n2cc(C(=O)O)cn2)cc2cc(-c3ccccc3)[nH]c12]

1-(7-Cyano-2-phenyl-1H-indol-5-yl)-pyrazole-4-carboxylic acid ethyl ester (0.02 g, 0.056 mmol) obtained in Preparation 56 was added to tetrahydrofuran (3.0 mL), methanol (3.0 mL) and 6N sodium hydroxide solution (1 mL), which were then reacted for 3 h at room temperature. After reaction, saturated ammonium chloride solution (5 mL) was added, and ethyl acetate (10 mL) was added. The organic layer was separated, dried over anhydrous magnesium sulfate and filtered. The solvent was removed and the residue was purified by column chromatography to give the title compound (0.01 g, 54% Yield).

NMR: $^1$H-NMR (CDCl$_3$) δ 8.42 (1H, s), 8.12 (1H, s), 8.10 (1H, s), 7.84 (1H, s), 7.77-7.46 (5H, m), 6.93 (1H, s)

Mass (EI) 329 (M$^+$+1)

Example 29

Synthesis of 1-(7-cyano-2-isopropyl-1H-indol-5-yl)-pyrazole-4-carboxylic acid

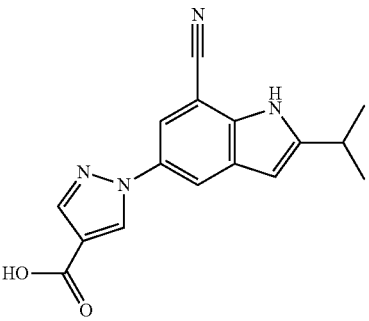 [SMILES: CC(C)c1cc2cc(-n3cc(C(=O)O)cn3)cc(C#N)c2[nH]1]

1-[4-Amino-3-cyano-5-(3-methyl-1-butinyl)-phenyl]-pyrazole-4-carboxylic acid ethyl ester (0.06 g, 0.18 mmol) obtained in Preparation 57 was reacted according to the same procedures as Preparation 56 and Example 28 in the order to give the title compound (0.015 g).

NMR: $^1$H-NMR (CDCl$_3$) δ 10.18 (1H, s), 8.32 (1H, s), 8.07 (1H, s), 7.94 (1H, s), 7.72 (1H, s), 6.33 (1H, s), 3.10 (1H, m), 1.35 (6H, d)

Mass (EI) 295 (M$^+$+1)

Example 30

Synthesis of 1-(7-cyano-2-methoxymethyl-1H-indol-5-yl)-pyrazole-4-carboxylic acid

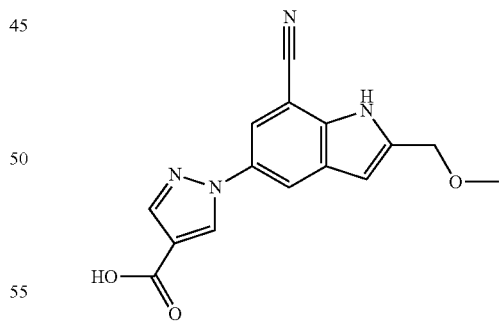

1-[4-Amino-3-cyano-5-(3-methoxy-1-propinyl)-phenyl]-pyrazole-4-carboxylic acid ethyl ester (0.16 g, 0.49 mmol) obtained in Preparation 58 was reacted according to the same procedures as Preparation 56 and Example 28 in the order to give the title compound (0.05 g).

NMR: $^1$H-NMR (CDCl$_3$) δ 10.95 (1H, s), 8.35 (1H, s), 8.04 (1H, s), 8.01 (1H, s), 7.78 (1H, d), 6.53 (1H, s), 4.57 (2H, s), 3.32 (3H, s)

Mass (EI) 297 (M$^+$+1)

Example 31

Synthesis of 1-(7-cyano-1H-indol-5-yl)-pyrazole-4-carboxylic acid

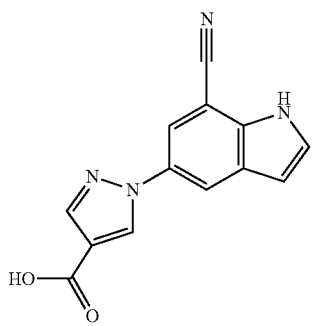 [SMILES: N#Cc1cc(-n2cc(C(=O)O)cn2)cc2cc[nH]c12]

1-(4-Amino-3-cyano-5-ethinyl-phenyl)-pyrazole-4-carboxylic acid ethyl ester (35 mg, 0.13 mmol) obtained in Preparation 60 was reacted according to the same procedures as Preparation 56 and Example 28 in the order to give the title compound (15 mg).

NMR: $^1$H-NMR (CDCl$_3$) δ 11.01 (1H, s), 8.35 (1H, s), 8.06 (2H, s), 7.82 (1H, s), 7.38 (1H, s), 6.61 (1H, s),

Mass (EI) 253 (M$^+$+1)

Experiment 1

Xanthine Oxidase Inhibition Activity

Xanthine oxidase originated from bovine milk was incubated for 3 min with test compounds, and the initial velocity of uric acid formation was determined by adding the substrate xanthine. The initial velocity of test compound at each concentration was converted to % inhibition rate on the basis of the initial velocity under the absence of the inhibitor, thereby the inhibitor concentration needed for 50% inhibition was calculated as IC$_{50}$ values. According to the present invention, compounds which show IC$_{50}$ values against xanthine oxidase from bovine milk in the level of nM were developed. Table 1 represents the inhibitory activities against xanthine oxidase of the test compounds.

TABLE 1

| Compound (Example No.) | IC$_{50}$ (nM) |
|---|---|
| 1 | 3.4 |
| 2 | 2.8 |
| 3 | 6 |
| 4 | 4.5 |
| 5 | 5 |
| 6 | 3.8 |
| 7 | 6.7 |
| 8 | 6.9 |
| 9 | 4.6 |
| 10 | 5.2 |
| 11 | 5.4 |
| 12 | 11.6 |
| 13 | 4.8 |
| 14 | 12 |
| 15 | 29200 |
| 16 | 21300 |
| 17 | 4.6 |
| 18 | 13 |
| 19 | 24 |
| 20 | 4.7 |

TABLE 1-continued

| Compound (Example No.) | IC$_{50}$ (nM) |
|---|---|
| 21 | 6.2 |
| 22 | 2.1 |
| 23 | 10 |
| 24 | 6.2 |
| 25 | 8.5 |
| 26 | 3940 |
| 27 | 11 |
| 28 | 24 |
| 29 | 5 |
| 30 | 17 |
| 31 | 40 |

Experiment 2

In Vivo Xanthine Oxidase Assay

Uric Acid-Lowering Activity in Plasma and Liver (Oxonic Acid-Induced High-Uric Acid Model in Rat)

In order to estimate the plasma uric acid-lowering ability of the compounds according to the present invention, experiments were carried out using oxonic acid-induced high-uric acid model.

Figure 2:
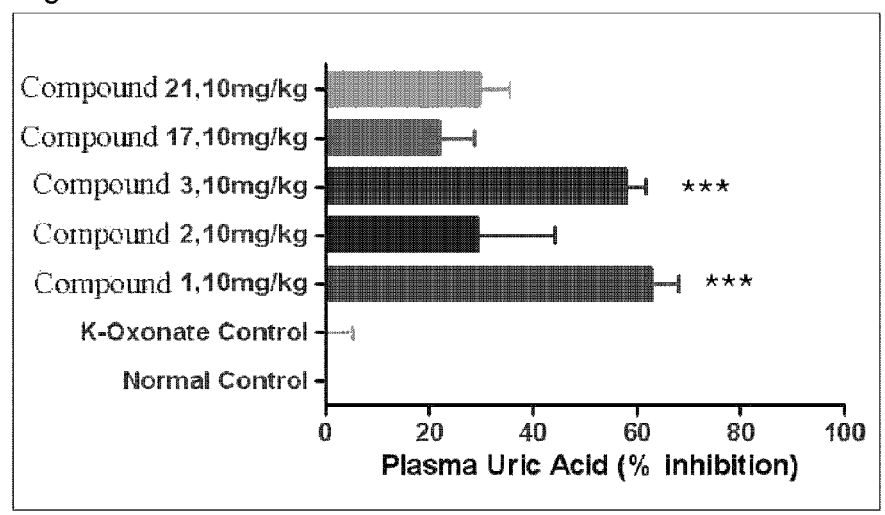
FIG. 2 is a graph showing the result of measuring the inhibitory rate (%) for uric acid in the plasma according to the procedure of Experiment 2 (***$P<0.001$, t-test, *$P<0.05$, **$P<0.01$ Dunnett's Multiple Comparison test).

300 mg/kg of potassium oxonate suspended in 0.8% carboxymethylcellulose solution was intraperitoneally administered to male SD rats of body weight 200 g (control group, compound administration group). 1 h after the oxonic acid administration, 10 mg/kg of test compounds dissolved in polyethyleneglycol 400:ethanol (2:1) solution were orally administered (compound administration group), and after the time period of 1 h blood was sampled. Plasma was separated from thus-obtained blood, and the uric acid concentration in the plasma was quantified utilizing LC-MS/MS. FIGS. 1 and 2 represent the results of plasma uric acid concentration and inhibition rate of plasma uric acid, respectively.

Through the present experiment, excellent plasma uric acid-lowering activity of the compounds according to the present invention was verified. For example, the uric acid inhibition rate of the compound of Example 1 (10 mg/kg) at 1 h after oral administration (putting the plasma uric acid level of normal group as 100% inhibition, and plasma uric acid level of control group as 0% inhibition) was 60%, a very excellent inhibitory effect.

As revealed by the above experiments, the compounds of formula (1) according to the present invention exert an excellent inhibitory effect on xanthine oxidase. Therefore, the compounds according to the present invention can be used as an agent for the treatment and prevention of the diseases associated with human xanthine oxidase such as hyperuricemia, gout, heart failure, cardiovascular disease, hypertension, diabetes, kidney disease, inflammation, articular disease, inflammatory bowel disease, etc.

Those skilled in the art will be able to make various applications and modifications on the basis of above disclosure within the scope of the present invention.

The invention claimed is:

1. A compound of the following formula (1):

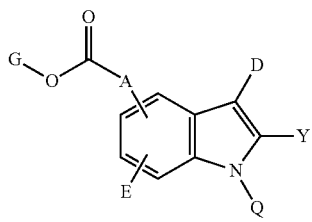

in the above formula (1)

A is selected from the following substituents A-i, A-ii, A-iii, A-iv, A-v, A-vi, A-vii and A-viii:

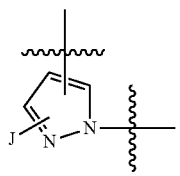 (A-i)

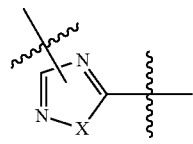 (A-ii)

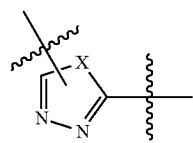 (A-iii)

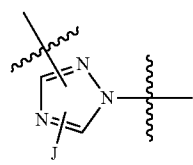 (A-iv)

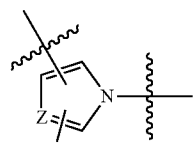 (A-v)

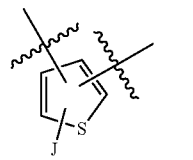 (A-vi)

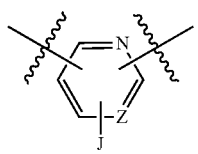 (A-vii)

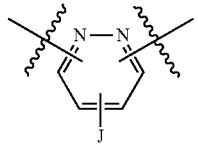 (A-viii)

wherein

J represents hydrogen, halogen, or halogen-substituted or unsubstituted $C_1$-$C_6$-alkyl, X represents O or S, Z represents C or N, E represents hydrogen, halogen, cyano, nitro, substituted or unsubstituted $C_1$-$C_6$-alkyl, or substituted or unsubstituted $C_1$-$C_6$-alkoxy, D represents halogen, cyano, nitro, halogen-substituted or unsubstituted $C_1$-$C_6$-alkyl, —CHO, or —CH=N—OH, Q is selected from the following substituents Q-i, Q-ii and Q-iii-1 to Q-iii-8:

(Q-i) hydrogen;

(Q-ii) $C_1$-$C_8$-alkyl which is unsubstituted or substituted by a group selected from halogen, hydroxyl, $C_3$-$C_7$-cycloalkyl and O—$R_6$ wherein $R_6$ represents $C_1$-$C_7$ alkyl;

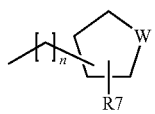 (Q-iii-1)

wherein W represents O or S, R7 represents hydrogen, or substituted or unsubstituted lower alkyl, and n denotes an integer of 0~3;

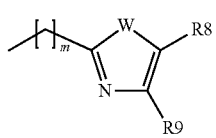 (Q-iii-2)

wherein W represents O or S, R8 and R9 each represent hydrogen or lower alkyl, and m denotes an integer of 1~3;

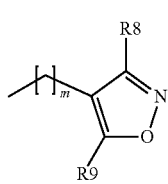 (Q-iii-3)

wherein R8 and R9 each represent hydrogen or lower alkyl, and m denotes an integer of 1~3;

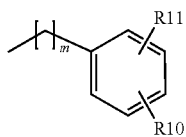
(Q-iii-4)

wherein R10 and R11 each represent hydrogen, halogen, lower alkoxy or lower alkyl, and m denotes an integer of 1~3;

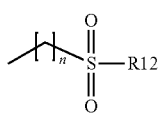
(Q-iii-5)

wherein R12 represents substituted or unsubstituted lower alkyl or aromatic group, and n denotes an integer of 0~3;

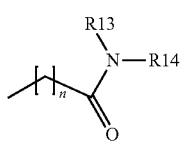
(Q-iii-6)

wherein R13 and R14 each represent substituted or unsubstituted lower alkyl, or together with N to which they are attached may form a 3~7 membered heterocycle, and n denotes an integer of 0~3;

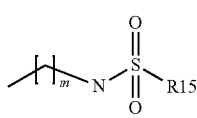
(Q-iii-7)

wherein R15 represents substituted or unsubstituted lower alkyl, and m denotes an integer of 1~3;

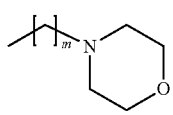
(Q-iii-8)

wherein m denotes an integer of 1~3;
Y represents hydrogen, halogen, substituted or unsubstituted, saturated or unsaturated, and straight-chain, branched or cyclic alkyl, substituted or unsubstituted $C_1$-$C_6$-alkoxy, or substituted or unsubstituted aromatic or heteroaromatic group, and
G represents hydrogen, or represents substituted or unsubstituted, saturated or unsaturated, and straight-chain, branched or cyclic alkyl,
or a pharmaceutically acceptable salt thereof.

2. The compound of claim 1 wherein A is selected from the following substituents A-i, A-ii, A-iii, A-iv, A-v, A-vi, A-vii and A-viii:

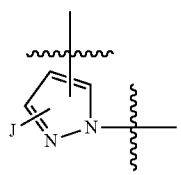
(A-i)

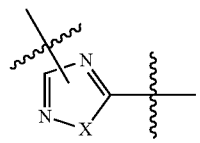
(A-ii)

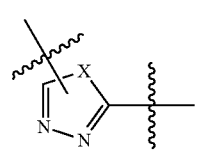
(A-iii)

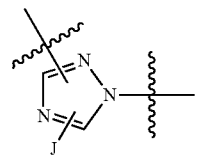
(A-iv)

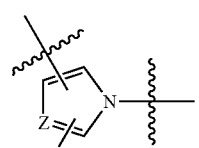
(A-v)

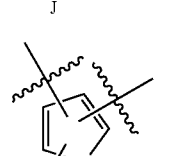
(A-vi)

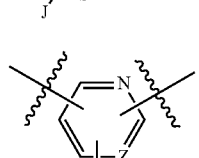
(A-vii)

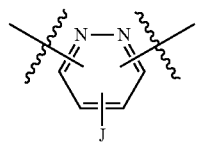
(A-viii)

wherein
J represents halogen-substituted or unsubstituted $C_1$-$C_4$-alkyl,
X represents O or S, and
Z represents C or N,
or a pharmaceutically acceptable salt thereof.

3. The compound of claim 1 wherein E represents hydrogen, halogen, cyano or nitro,
or a pharmaceutically acceptable salt thereof.

4. The compound of claim 1 wherein D represents halogen, cyano, nitro, or —CHO,
or a pharmaceutically acceptable salt thereof.

5. The compound of claim 1 wherein Y represents hydrogen, $C_1$-$C_7$-alkyl, $C_1$-$C_7$-alkoxy-$C_1$-$C_7$-alkyl, or aromatic group, or a pharmaceutically acceptable salt thereof.

6. The compound of claim 1 wherein G represents hydrogen, or a pharmaceutically acceptable salt thereof.

7. The compound of claim 1 wherein

A is selected from the following substituents A-i, A-iv, A-v, A-vi and A-vii:

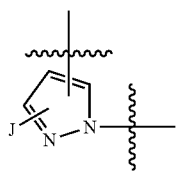
(A-i)

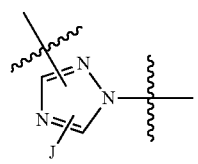
(A-iv)

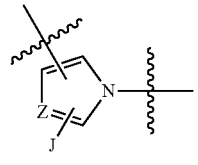
(A-v)

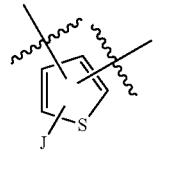
(A-vi)

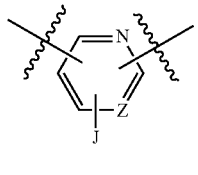
(A-vii)

wherein

J represents halogen-substituted or unsubstituted $C_1$-$C_4$-alkyl,

X represents O or S, and

Z represents C or N,

E represents hydrogen or cyano,

D represents cyano or nitro,

Q is selected from the following substituents Q-i, Q-ii and Q-iii-1:

(Q-i) hydrogen;

(Q-ii) $C_1$-$C_8$-alkyl which is unsubstituted or substituted by a group selected from halogen, $C_3$-$C_7$-cycloalkyl and O—$R_6$ wherein $R_6$ represents $C_1$-$C_4$-alkyl;

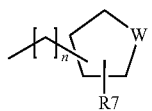
(Q-iii-1)

wherein W represents O or S, R7 represents hydrogen or $C_1$-$C_4$-alkyl, and n denotes an integer of 0~3;

Y represents hydrogen, $C_1$-$C_4$-alkyl, $C_1$-$C_4$-alkoxy-$C_1$-$C_4$-alkyl or phenyl, and G represents hydrogen, or a pharmaceutically acceptable salt thereof.

8. A compound which is selected from the following group:
1-(3-cyano-1-isopropyl-indol-5-yl)pyrazole-4-carboxylic acid;
1-[3-cyano-1-(cyclopropylmethyl)indol-5-yl]pyrazole-4-carboxylic acid;
1-[3-cyano-1-cyclopropyl-indol-5-yl]pyrazole-4-carboxylic acid;
1-(3-cyano-1-isobutyl-indol-5-yl)pyrazole-4-carboxylic acid;
1-[3-cyano-1-(2,2-dimethylpropyl)indol-5-yl]pyrazole-4-carboxylic acid;
1-[3-cyano-1-(2-methoxyethyl)indol-5-yl]pyrazole-4-carboxylic acid;
1-(3-cyano-1-sec-butyl-indol-5-yl)-pyrazole-4-carboxylic acid;
1-[3-cyano-1-cyclobutyl-indol-5-yl]pyrazole-4-carboxylic acid;
1-(3-cyano-1-cyclopentyl-indol-5-yl)-pyrazole-4-carboxylic acid;
1-[3-cyano-1-(1-fluoropropan-2-yl)-indol-5-yl]-pyrazole-4-carboxylic acid;
1-[3-cyano-1-(tetrahydrofuran-3-yl)-indol-5-yl]-pyrazole-4-carboxylic acid;
1-[3-cyano-1-isopropyl-indol-5-yl]-3-methyl-pyrazole-4-carboxylic acid;
1-[3-cyano-1-(cyclopropylmethyl)indol-5-yl]-3-methyl-pyrazole-4-carboxylic acid;
1-[3-cyano-1-(2-methoxyethyl)indol-5-yl]-3-methyl-pyrazole-4-carboxylic acid;
1-[3-cyano-1-isopropyl-indol-5-yl]-3-(trifluoromethyl)pyrazole-4-carboxylic acid;
1-[3-cyano-1-(cyclopropylmethyl)indol-5-yl]-3-(trifluoromethyl)pyrazole-4-carboxylic acid;
1-(1-isopropyl-3-nitro-indol-5-yl)pyrazole-4-carboxylic acid;
1-(3-cyano-1-isopropyl-indol-5-yl)-1,2,4-triazole-3-carboxylic acid;
1-(3-cyano-1-isopropyl-indol-5-yl)imidazole-4-carboxylic acid;
5-(3-cyano-1-isopropyl-indol-5-yl)-thiophene-2-carboxylic acid;
2-(3-cyano-1-isopropyl-indol-5-yl)isonicotinic acid;
2-[3-cyano-1-(cyclopropylmethyl)-indol-5-yl]isonicotinic acid;
2-[3-cyano-1-(tetrahydrofuran-3-yl)-indol-5-yl]isonicotinic acid;
2-[3-cyano-1-(1-fluoropropan-2-yl)-indol-5-yl]isonicotinic acid;
2-[3-cyano-1-(2-methoxyethyl)-indol-5-yl]isonicotinic acid;
2-(3-cyano-1-isopropyl-indol-5-yl)-6-methylisonicotinic acid;
2-(1-isopropyl-3-nitro-indol-5-yl)isonicotinic acid;

1-(7-cyano-2-phenyl-1H-indol-5-yl)-pyrazole-4-carboxylic acid;

1-(7-cyano-2-isopropyl-1H-indol-5-yl)-pyrazole-4-carboxylic acid;

1-(7-cyano-2-methoxymethyl-1H-indol-5-yl)-pyrazole-4-carboxylic acid; and 1-(7-cyano-1H-indol-5-yl)-pyrazole-4-carboxylic acid, or a pharmaceutically acceptable salt thereof.

9. A process for preparing the compound of formula (1), or a pharmaceutically acceptable salt thereof according to claim 1 characterized by the following Reaction Scheme (1):

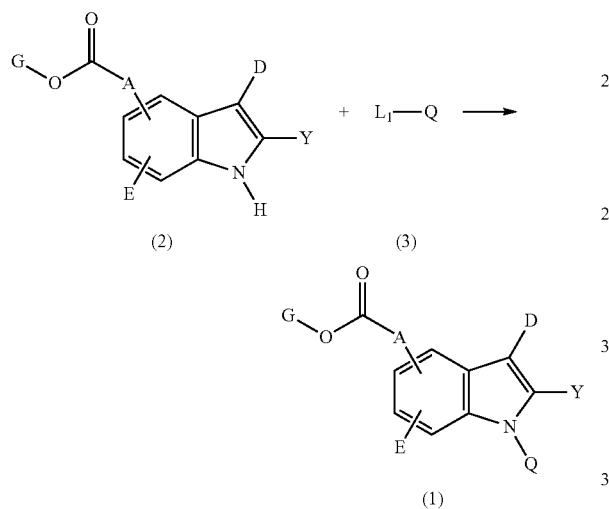

in the above Reaction Scheme (1),

A, D, E, G, Y and Q are as defined in claim 1, provided that Q is not hydrogen, and $L_1$ represents a leaving group.

10. A process for preparing the compound of formula (1), or a pharmaceutically acceptable salt thereof according to claim 1 characterized by the following Reaction Scheme (2):

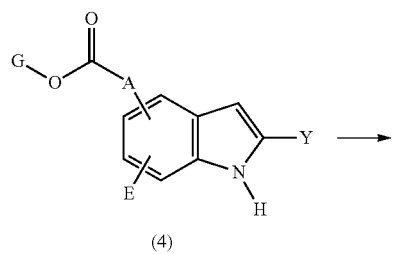

in the above Reaction Scheme (2),

A, D, E, G and Y are as defined in claim 1.

11. The process of claim 10, wherein the compound of formula (4) used as a starting material is prepared according to the following Reaction Scheme (3):

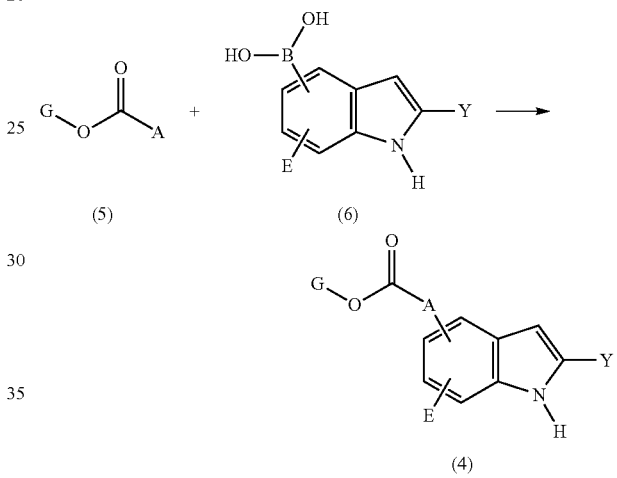

in the above Reaction Scheme (3), A, E, G and Y are as defined in claim 1.

12. A pharmaceutical composition for the inhibition of xanthine oxidase, which comprises (a) a therapeutically effective amount of the compound of formula (1), or a pharmaceutically acceptable salt thereof according to claim 1; and (b) a pharmaceutically acceptable carrier, a diluent, an excipient or a combination thereof.

13. The composition of claim 12, which is used for the treatment of diseases associated with human xanthine oxidase.

14. The composition of claim 13 wherein the diseases associated with human xanthine oxidase is selected from the group consisting of hyperuricemia, gout, heart failure, cardiovascular disease, hypertension, diabetes, complications of diabetes, kidney disease, inflammation, articular disease and inflammatory bowel disease.

15. The composition of claim 14 wherein the complications of diabetes is selected from the group consisting of hyperlipidemia, atherosclerosis, obesity, hypertension, retinosis and renal failure.

* * * * *